(12) United States Patent
Frank et al.

(10) Patent No.: US 9,439,623 B2
(45) Date of Patent: *Sep. 13, 2016

(54) SURGICAL PLANNING SYSTEM AND NAVIGATION SYSTEM

(75) Inventors: Kevin J. Frank, Lafayette, CO (US); Jason A. Case, Longmont, CO (US); Casey M. Ladtkow, Westminster, CO (US)

(73) Assignee: Covidien LP, Mansfield, MA (US)

( * ) Notice: Subject to any disclaimer, the term of this patent is extended or adjusted under 35 U.S.C. 154(b) by 173 days.

This patent is subject to a terminal disclaimer.

(21) Appl. No.: 13/477,417

(22) Filed: May 22, 2012

(65) Prior Publication Data

US 2013/0317353 A1   Nov. 28, 2013

(51) Int. Cl.
*A61B 8/00* (2006.01)
*G06K 9/00* (2006.01)
(Continued)

(52) U.S. Cl.
CPC ......... *A61B 8/0841* (2013.01); *A61B 18/1815* (2013.01); *A61B 90/04* (2016.02); *G06T 7/0046* (2013.01); *A61B 8/565* (2013.01); *A61B 18/1477* (2013.01); *A61B 2017/00477* (2013.01); *A61B 2018/00577* (2013.01); *A61B 2018/1425* (2013.01); *A61B 2018/183* (2013.01); *A61B 2018/1869* (2013.01); *A61B 2034/104* (2016.02); *A61B 2090/0463* (2016.02); *A61B 2090/0472* (2016.02); *A61B 2090/0481* (2016.02); *A61B 2090/3983* (2016.02);
(Continued)

(58) Field of Classification Search
CPC ................................................ A61B 19/5244

USPC ........................................................ 600/426
See application file for complete search history.

(56) References Cited

U.S. PATENT DOCUMENTS 5,515,160 A    5/1996  Schulz et al.
5,528,699 A    6/1996  Obata et al.
(Continued)

FOREIGN PATENT DOCUMENTS

CN    1788693 A    6/2006
CN    101249001 A   8/2008
(Continued)

OTHER PUBLICATIONS

International Search Report dated Aug. 21, 2013, corresponding to International Application No. PCT/US2013/041842; 4 pages.
(Continued)

*Primary Examiner* — Patricia Park

(57) ABSTRACT

The present disclosure is directed to a planning and navigation system. The planning system includes a memory configured to store a plurality of images and a controller configured to render the plurality of images in three dimensions, automatically segment the plurality of images to demarcate a target area, and automatically determine a treatment plan based on the target area. The navigation system includes an ultrasound device having a fiducial pattern that obtains an ultrasound image, a surgical device having a image capture device that captures an image of the fiducial pattern, and a controller that receives the ultrasound image and the fiducial image. The controller determines a position of the surgical device based on the fiducial image. The planning and navigation system also includes a controller that receives data from the planning system and the navigation system and a display configured to display the received information.

16 Claims, 22 Drawing Sheets

(51) Int. Cl.
*A61B 8/08* (2006.01)
*A61B 18/18* (2006.01)
*G06T 7/00* (2006.01)
*A61B 18/14* (2006.01)
*A61B 17/00* (2006.01)
*A61B 18/00* (2006.01)

(52) U.S. Cl.
CPC ............ *G06T 2207/30004* (2013.01); *G06T 2207/30208* (2013.01); *G06T 2207/30244* (2013.01)

(56) References Cited

U.S. PATENT DOCUMENTS

| | | | |
|---|---|---|---|
| 5,776,062 | A | 7/1998 | Nields |
| 5,788,636 | A | 8/1998 | Curley |
| 5,799,099 | A | 8/1998 | Wang et al. |
| 5,810,008 | A | 9/1998 | Dekel et al. |
| 5,817,022 | A | 10/1998 | Vesely |
| 5,825,908 | A | 10/1998 | Pieper et al. |
| 5,836,954 | A | 11/1998 | Heilbrun et al. |
| 5,842,473 | A | 12/1998 | Fenster et al. |
| 5,873,822 | A | 2/1999 | Ferre et al. |
| 5,891,030 | A | 4/1999 | Johnson et al. |
| 5,902,239 | A | 5/1999 | Buurman |
| 5,953,013 | A | 9/1999 | Shimizu |
| 5,954,648 | A | 9/1999 | Van Der Brug |
| 5,957,844 | A | 9/1999 | Dekel et al. |
| 5,967,980 | A | 10/1999 | Ferre et al. |
| 6,002,808 | A | 12/1999 | Freeman |
| 6,006,126 | A | 12/1999 | Cosman |
| 6,019,724 | A | 2/2000 | Gronningsaeter et al. |
| 6,052,477 | A | 4/2000 | Wang et al. |
| 6,081,577 | A | 6/2000 | Webber |
| 6,112,112 | A | 8/2000 | Gilhuijs et al. |
| 6,112,113 | A | 8/2000 | Van Der Brug et al. |
| 6,119,033 | A | 9/2000 | Spigelman et al. |
| 6,165,181 | A | 12/2000 | Heilbrun et al. |
| 6,167,296 | A | 12/2000 | Shahidi |
| 6,195,444 | B1 | 2/2001 | Simanovsky et al. |
| 6,203,497 | B1 | 3/2001 | Dekel et al. |
| 6,216,029 | B1 | 4/2001 | Paltieli |
| 6,226,542 | B1 | 5/2001 | Reisfeld |
| 6,259,943 | B1 | 7/2001 | Cosman et al. |
| 6,285,902 | B1 | 9/2001 | Kienzle et al. |
| 6,298,262 | B1 | 10/2001 | Franck et al. |
| 6,301,495 | B1 | 10/2001 | Gueziec et al. |
| 6,332,089 | B1 | 12/2001 | Acker et al. |
| 6,334,847 | B1 | 1/2002 | Fenster et al. |
| 6,338,716 | B1 | 1/2002 | Hossack et al. |
| 6,341,231 | B1 | 1/2002 | Ferre et al. |
| 6,343,936 | B1 | 2/2002 | Kaufman et al. |
| 6,379,302 | B1 | 4/2002 | Kessman et al. |
| 6,381,483 | B1 | 4/2002 | Hareyama et al. |
| 6,440,071 | B1 | 8/2002 | Slayton et al. |
| 6,442,417 | B1 | 8/2002 | Shahidi et al. |
| 6,466,815 | B1 | 10/2002 | Saito et al. |
| 6,470,207 | B1 | 10/2002 | Simon et al. |
| 6,477,275 | B1 | 11/2002 | Melikian et al. |
| 6,487,432 | B2 | 11/2002 | Slack |
| 6,505,065 | B1 | 1/2003 | Yanof et al. |
| 6,529,758 | B2 | 3/2003 | Shahidi |
| 6,539,247 | B2 | 3/2003 | Spetz |
| 6,540,679 | B2 | 4/2003 | Slayton et al. |
| 6,546,279 | B1 | 4/2003 | Bova et al. |
| 6,553,152 | B1 | 4/2003 | Miller et al. |
| 6,574,493 | B2 | 6/2003 | Rasche et al. |
| 6,612,980 | B2 | 9/2003 | Chen et al. |
| 6,669,635 | B2 | 12/2003 | Kessman et al. |
| 6,675,032 | B2 | 1/2004 | Chen et al. |
| 6,694,163 | B1 | 2/2004 | Vining |
| 6,711,429 | B1 | 3/2004 | Gilboa et al. |
| 6,724,930 | B1 | 4/2004 | Kosaka et al. |
| 6,731,966 | B1 | 5/2004 | Spigelman et al. |
| 6,733,458 | B1 | 5/2004 | Steins et al. |
| 6,751,361 | B1 | 6/2004 | Wagman |
| 6,754,374 | B1 | 6/2004 | Miller et al. |
| 6,772,002 | B2 | 8/2004 | Schmidt et al. |
| 6,812,933 | B1 | 11/2004 | Silver |
| 6,892,090 | B2 | 5/2005 | Verard et al. |
| 6,909,913 | B2 | 6/2005 | Vining |
| 6,920,347 | B2 | 7/2005 | Simon et al. |
| 6,925,319 | B2 | 8/2005 | McKinnon |
| 6,947,786 | B2 | 9/2005 | Simon et al. |
| 6,961,405 | B2 | 11/2005 | Scherch |
| 6,968,224 | B2 | 11/2005 | Kessman et al. |
| 6,969,352 | B2 | 11/2005 | Chiang et al. |
| 6,973,202 | B2 | 12/2005 | Mostafavi |
| 7,035,461 | B2 | 4/2006 | Luo et al. |
| 7,043,055 | B1 | 5/2006 | Silver |
| 7,043,064 | B2 | 5/2006 | Paik et al. |
| 7,050,845 | B2 | 5/2006 | Vilsmeier |
| 7,161,596 | B2 | 1/2007 | Hoile |
| 7,171,255 | B2 | 1/2007 | Holupka et al. |
| 7,204,254 | B2 | 4/2007 | Riaziat et al. |
| 7,215,990 | B2 | 5/2007 | Fesner et al. |
| 7,251,352 | B2 | 7/2007 | Sauer et al. |
| 7,259,762 | B2 | 8/2007 | Tanacs et al. |
| 7,302,288 | B1 | 11/2007 | Schellenberg |
| 7,333,644 | B2 | 2/2008 | Jerebko et al. |
| 7,343,026 | B2 | 3/2008 | Niwa |
| 7,379,572 | B2 | 5/2008 | Yoshida et al. |
| 7,383,073 | B1 | 6/2008 | Abovitz et al. |
| 7,450,749 | B2 | 11/2008 | Rouet et al. |
| 7,452,357 | B2 | 11/2008 | Vlegele et al. |
| 7,457,443 | B2 | 11/2008 | Persky |
| 7,491,198 | B2 | 2/2009 | Kockro |
| 7,492,930 | B2 | 2/2009 | Leitner et al. |
| 7,496,173 | B2 | 2/2009 | Goldman et al. |
| 7,499,743 | B2 | 3/2009 | Vass et al. |
| 7,519,218 | B2 | 4/2009 | Takemoto et al. |
| 7,536,041 | B2 | 5/2009 | Pekar et al. |
| 7,567,697 | B2 | 7/2009 | Mostafavi |
| 7,570,987 | B2 | 8/2009 | Raabe et al. |
| 7,581,191 | B2 | 8/2009 | Rice et al. |
| 7,593,505 | B2 | 9/2009 | Saracen et al. |
| 7,623,250 | B2 | 11/2009 | Moctezuma de la Barrera et al. |
| 7,630,753 | B2 | 12/2009 | Simon et al. |
| 7,636,420 | B2 | 12/2009 | Spies et al. |
| 7,639,853 | B2 | 12/2009 | Olivera et al. |
| 7,643,663 | B2 | 1/2010 | Wiemker et al. |
| 7,672,705 | B2 | 3/2010 | Lachaine et al. |
| 7,689,019 | B2 | 3/2010 | Boese et al. |
| 7,780,084 | B2 | 8/2010 | Zhang et al. |
| 7,809,184 | B2 | 10/2010 | Neubauer et al. |
| 7,831,082 | B2 | 11/2010 | Holsing et al. |
| 7,844,087 | B2 | 11/2010 | Ray et al. |
| 7,853,305 | B2 | 12/2010 | Simon et al. |
| 7,856,130 | B2 | 12/2010 | Suri et al. |
| 7,860,331 | B2 | 12/2010 | Lal et al. |
| 7,860,548 | B2 | 12/2010 | McIntyre et al. |
| 7,873,400 | B2 | 1/2011 | Moctezuma de la Barrera et al. |
| 7,874,987 | B2 | 1/2011 | Altmann et al. |
| 7,876,937 | B2 | 1/2011 | Schildkraut et al. |
| 7,876,939 | B2 | 1/2011 | Yankelevitz et al. |
| 7,876,942 | B2 | 1/2011 | Gilboa |
| 7,892,224 | B2 | 2/2011 | Hartlep et al. |
| 7,894,663 | B2 | 2/2011 | Berg et al. |
| 7,899,513 | B2 | 3/2011 | Phillips et al. |
| 7,907,772 | B2 | 3/2011 | Wang et al. |
| 7,912,258 | B2 | 3/2011 | Warmath et al. |
| 7,916,918 | B2 | 3/2011 | Suri et al. |
| 7,920,911 | B2 | 4/2011 | Hoshino et al. |
| 7,953,265 | B2 | 5/2011 | Sirohey et al. |
| 7,957,572 | B2 | 6/2011 | Von Berg et al. |
| 7,970,174 | B2 | 6/2011 | Goldbach |
| 8,000,442 | B2 | 8/2011 | Lachaine et al. |
| 8,010,180 | B2 | 8/2011 | Quaid et al. |
| 8,019,133 | B2 | 9/2011 | Knoplioch et al. |
| 8,023,712 | B2 | 9/2011 | Ikuma et al. |
| 8,023,734 | B2 | 9/2011 | Jolly et al. |
| 8,036,435 | B2 | 10/2011 | Partain et al. |
| 8,045,778 | B2 | 10/2011 | Blaffert et al. |
| 8,046,052 | B2 | 10/2011 | Verard et al. |

(56) References Cited

U.S. PATENT DOCUMENTS

| | | |
|---|---|---|
| 2003/0135115 A1 | 7/2003 | Burdette et al. |
| 2003/0151665 A1* | 8/2003 | Uchiyama ............... 348/187 |
| 2003/0163142 A1 | 8/2003 | Paltieli et al. |
| 2004/0015070 A1 | 1/2004 | Liang et al. |
| 2004/0034297 A1 | 2/2004 | Darrow et al. |
| 2005/0215854 A1* | 9/2005 | Ozaki et al. ............. 600/109 |
| 2006/0229594 A1 | 10/2006 | Francischelli et al. |
| 2007/0238961 A1 | 10/2007 | Vilsmeier et al. |
| 2008/0063136 A1 | 3/2008 | Ohyu et al. |
| 2008/0081982 A1 | 4/2008 | Simon et al. |
| 2008/0097186 A1 | 4/2008 | Biglieri et al. |
| 2008/0119712 A1 | 5/2008 | Lloyd |
| 2008/0123921 A1 | 5/2008 | Gielen et al. |
| 2008/0123927 A1 | 5/2008 | Miga et al. |
| 2008/0167547 A1 | 7/2008 | Bova et al. |
| 2008/0200794 A1 | 8/2008 | Teichman et al. |
| 2008/0200926 A1 | 8/2008 | Verard et al. |
| 2008/0200927 A1 | 8/2008 | Hartmann et al. |
| 2008/0208041 A1* | 8/2008 | Gilboa ............... 600/426 |
| 2008/0214922 A1 | 9/2008 | Hartmann et al. |
| 2008/0232656 A1 | 9/2008 | Voegele |
| 2008/0242978 A1* | 10/2008 | Simon et al. ............. 600/426 |
| 2008/0262345 A1* | 10/2008 | Fichtinger et al. ......... 600/426 |
| 2008/0285854 A1 | 11/2008 | Kotake et al. |
| 2009/0028436 A1* | 1/2009 | Yoshino et al. ............ 382/190 |
| 2009/0124896 A1 | 5/2009 | Haras |
| 2009/0198126 A1 | 8/2009 | Klingenbeck-Regn |
| 2009/0221908 A1 | 9/2009 | Glossop |
| 2009/0292201 A1 | 11/2009 | Kruecker |
| 2009/0312629 A1 | 12/2009 | Razzaque et al. |
| 2010/0063392 A1 | 3/2010 | Nishina et al. |
| 2010/0063496 A1 | 3/2010 | Trovato et al. |
| 2010/0076305 A1 | 3/2010 | Maier-Hein et al. |
| 2010/0121189 A1 | 5/2010 | Ma et al. |
| 2010/0121190 A1 | 5/2010 | Pagoulatos et al. |
| 2010/0168763 A1 | 7/2010 | Zhao et al. |
| 2010/0179529 A1 | 7/2010 | Podhajsky et al. |
| 2010/0208963 A1* | 8/2010 | Kruecker et al. ............ 382/131 |
| 2010/0217117 A1 | 8/2010 | Glossop et al. |
| 2010/0249771 A1 | 9/2010 | Pearson et al. |
| 2010/0259474 A1* | 10/2010 | Hildreth ............... 345/156 |
| 2010/0268223 A1* | 10/2010 | Coe et al. ............... 606/41 |
| 2010/0274124 A1 | 10/2010 | Jascob et al. |
| 2010/0277655 A1* | 11/2010 | Sun ............... 348/744 |
| 2010/0295931 A1 | 11/2010 | Schmidt |
| 2010/0298705 A1 | 11/2010 | Pelissier et al. |
| 2010/0312103 A1* | 12/2010 | Gorek et al. ............ 600/425 |
| 2010/0322489 A1 | 12/2010 | Tizhoosh et al. |
| 2011/0015628 A1 | 1/2011 | Dalal et al. |
| 2011/0118596 A1 | 5/2011 | Vining et al. |
| 2011/0129154 A1 | 6/2011 | Shimodaira |
| 2011/0137156 A1 | 6/2011 | Razzaque et al. |
| 2011/0137168 A1 | 6/2011 | Lee et al. |
| 2011/0160569 A1 | 6/2011 | Cohen et al. |
| 2011/0251483 A1 | 10/2011 | Razzaque et al. |
| 2012/0050258 A1 | 3/2012 | Kay et al. |
| 2012/0136242 A1 | 5/2012 | Qi et al. |
| 2012/0277585 A1* | 11/2012 | Koenig et al. ............ 600/437 |
| 2013/0142410 A1* | 6/2013 | Dwivedi et al. ............ 382/131 |

FOREIGN PATENT DOCUMENTS

| | | |
|---|---|---|
| CN | 201422889 Y | 3/2010 |
| EP | 1 649 822 A1 | 4/2006 |
| WO | WO 95/15729 A1 | 6/1995 |
| WO | WO 97/03609 A1 | 2/1997 |
| WO | WO 01/39124 A2 | 5/2001 |
| WO | WO 2006/089426 A1 | 8/2006 |
| WO | 2007113815 A2 | 10/2007 |
| WO | WO 2008/017051 A2 | 2/2008 |
| WO | WO 2008/058520 A2 | 5/2008 |
| WO | 2012025842 A2 | 3/2012 |
| WO | WO 2012/066446 A1 | 5/2012 |

OTHER PUBLICATIONS

European Search Report dated Oct. 10, 2013, corresponding to European Application No. EP 13 16 8705; 8 pages.
European Search Report dated Oct. 8, 2013 corresponding to European Application No. EP 13 16 8706; 8 pages.
European Search Report dated Aug. 23, 2013, corresponding to European Application No. EP 13 16 8707; 9 pages.
European Search Report dated Aug. 23, 2013, corresponding to European Application No. EP 13 16 8516; 15 pages.
Kosaka A. et al. "Augmented Reality System for Surgical Navigation Using Robust Target Vision", Proceedings 2000 IEEE Conference on Computer Vision and Pattern Recognition. CVPR 2000. Hilton Head Island, SC, Jun. 13-15, 2000, pp. 187-194.
European Search Report dated Oct. 23, 2013 for EP 13 17 6292.
U.S. Appl. No. 13/477,374, filed May 22, 2012, Jason A. Case et al.
U.S. Appl. No. 13/477,406, filed May 22, 2012, Kevin Frank et al.
U.S. Appl. No. 13/477,291, filed May 22, 2012, Jason A. Case et al.
U.S. Appl. No. 13/477,279, filed May 22, 2012, Kevin Frank et al.
U.S. Appl. No. 13/477,395, filed May 22, 2012, Jason A. Case et al.
European Search report issued in corresponding application No. EP 15 17 6466 on Jan. 7, 2016.
Office Action issued in corresponding Chinese Application No. 201310333790.0 on May 23, 2016. (16 pages).
Office Action issued in corresponding Chinese Application No. 201310361572.8 on Jun. 1, 2016. (9 pages).

\* cited by examiner

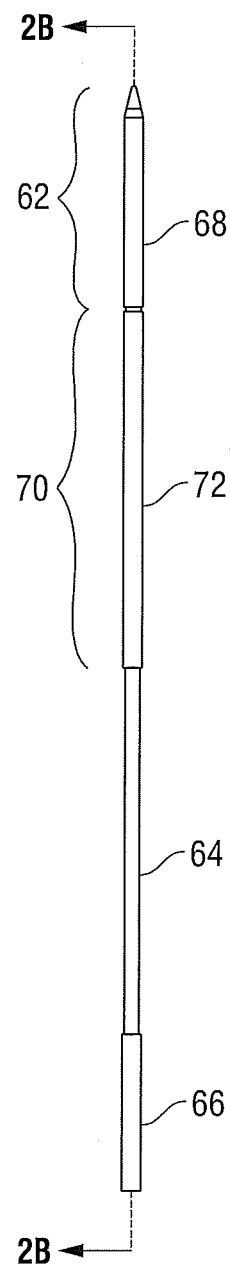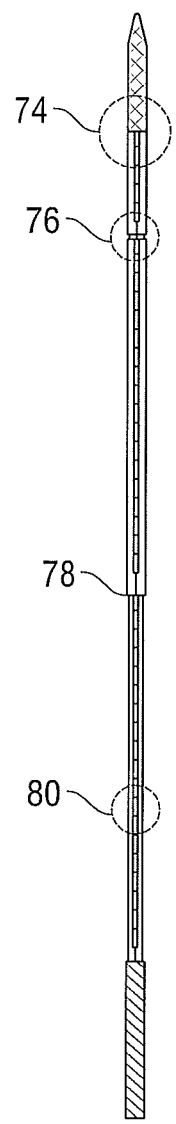
FIG. 2A     FIG. 2B

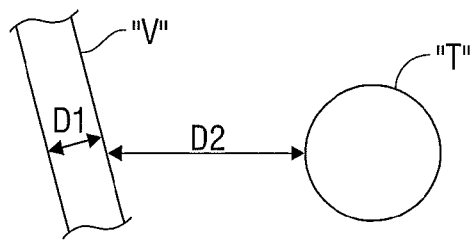
FIG. 11A
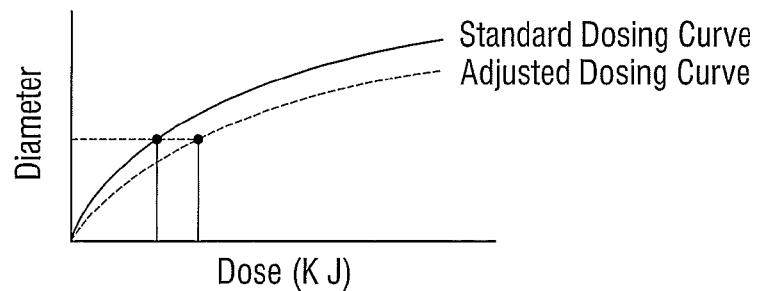
FIG. 11B
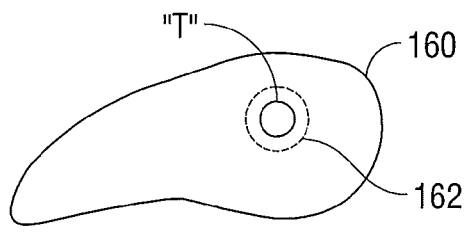   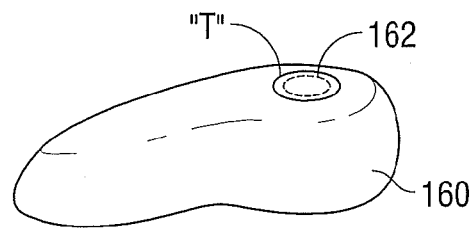
FIG. 12A   FIG. 12B
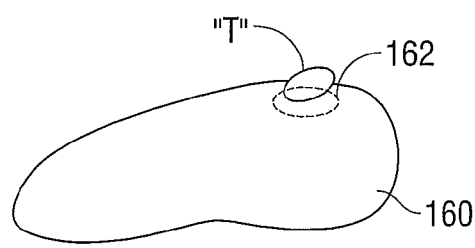
FIG. 12C

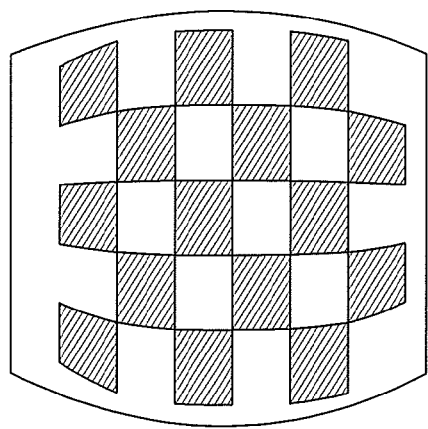 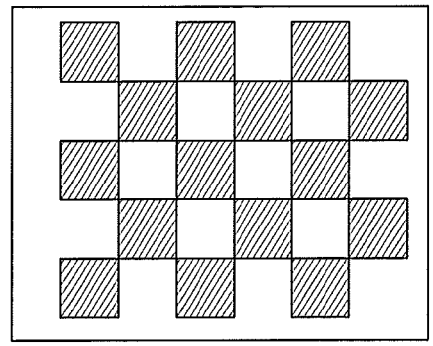
FIG. 16A  FIG. 16B
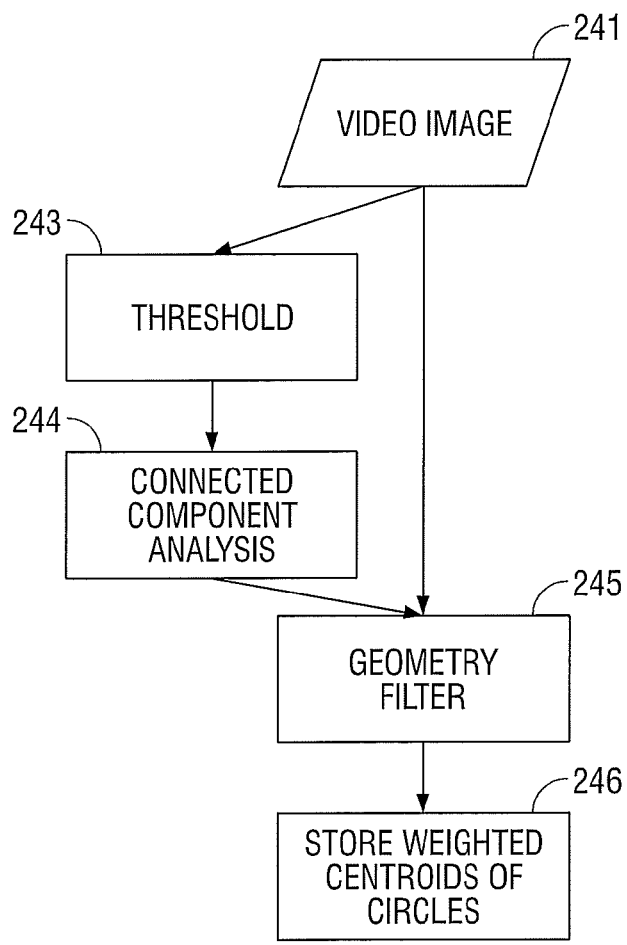
FIG. 17

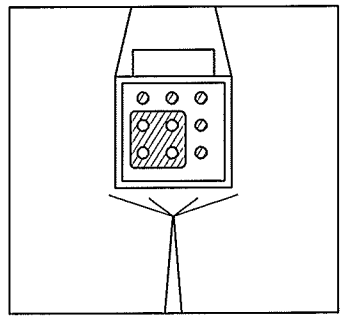
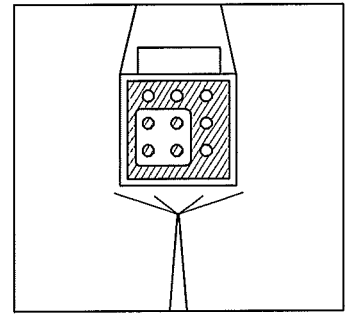
FIG. 20A          FIG. 20B
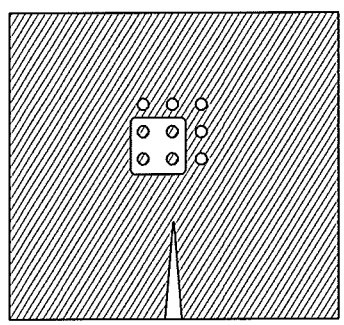
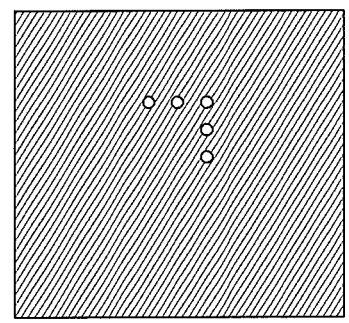
FIG. 20C          FIG. 20D

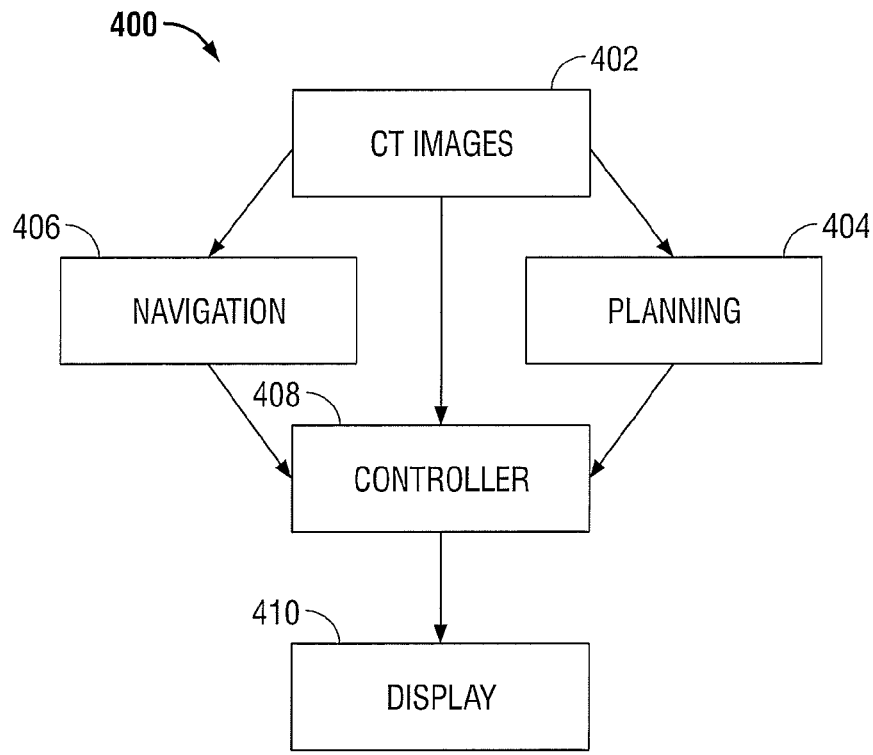
FIG. 24
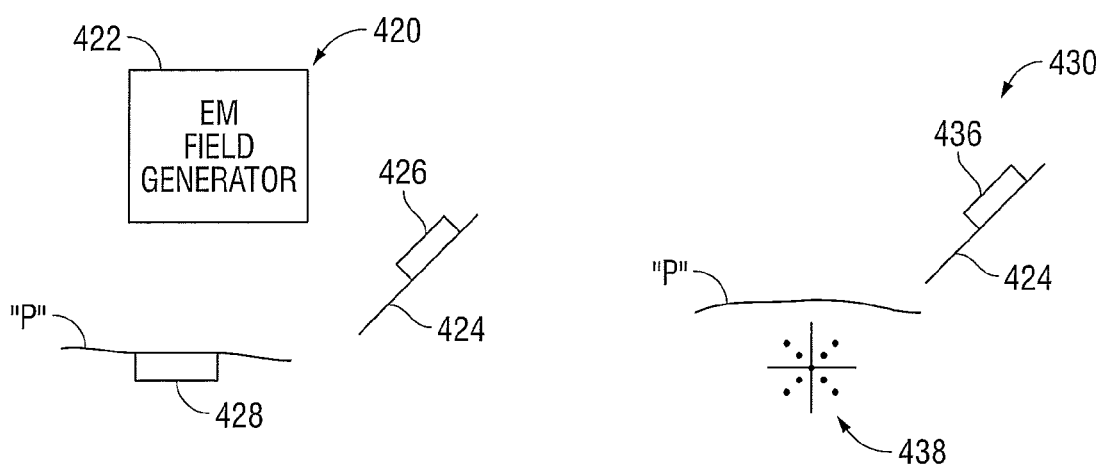
FIG. 25A  FIG. 25B

SURGICAL PLANNING SYSTEM AND NAVIGATION SYSTEM

BACKGROUND

1. Technical Field

The present disclosure relates to the surgical procedures. More specifically, the present disclosure is directed to the use of a planning system to determine a treatment plan and a navigation system to effect the treatment plan.

2. Background of the Related Art

Electrosurgical devices have become widely used. Electrosurgery involves the application of thermal and/or electrical energy to cut, dissect, ablate, coagulate, cauterize, seal or otherwise treat biological tissue during a surgical procedure. Electrosurgery is typically performed using a handpiece including a surgical device (e.g., end effector or ablation probe) that is adapted to transmit energy to a tissue site during electrosurgical procedures, a remote electrosurgical generator operable to output energy, and a cable assembly operatively connecting the surgical device to the remote generator.

Treatment of certain diseases requires the destruction of malignant tissue growths, e.g., tumors. In the treatment of diseases such as cancer, certain types of tumor cells have been found to denature at elevated temperatures that are slightly lower than temperatures normally injurious to healthy cells. Known treatment methods, such as hyperthermia therapy, typically involving heating diseased cells to temperatures above 41° C. while maintaining adjacent healthy cells below the temperature at which irreversible cell destruction occurs. These methods may involve applying electromagnetic radiation to heat, ablate and/or coagulate tissue. There are a number of different types of electrosurgical apparatus that can be used to perform ablation procedures.

Minimally invasive tumor ablation procedures for cancerous or benign tumors may be performed using two dimensional (2D) preoperative computed tomography (CT) images and an "ablation zone chart" which typically describes the characteristics of an ablation needle in an experimental, ex vivo tissue across a range of input parameters (power, time). Energy dose (power, time) can be correlated to ablation tissue effect (volume, shape) for a specific design. It is possible to control the energy dose delivered to tissue through microwave antenna design, for example, an antenna choke may be employed to provide a known location of microwave transfer from device into tissue. In another example, dielectric buffering enables a relatively constant delivery of energy from the device into the tissue independent of differing or varying tissue properties.

After a user determines which ablation needle should be used to effect treatment of a target, the user performs the treatment with ultrasound guidance. Typically, a high level of skill is required to place a surgical device into a target identified under ultrasound. Of primary importance is the ability to choose the angle and entry point required to direct the device toward the ultrasound image plane (e.g., where the target is being imaged).

Ultrasound-guided intervention involves the use of real-time ultrasound imaging (transabdominal, intraoperative, etc.) to accurately direct surgical devices to their intended target. This can be performed by percutaneous application and/or intraoperative application. In each case, the ultrasound system will include a transducer that images patient tissue and is used to identify the target and to anticipate and/or follow the path of an instrument toward the target.

Ultrasound-guided interventions are commonly used today for needle biopsy procedures to determine malignancy of suspicious lesions that have been detected (breast, liver, kidney, and other soft tissues). Additionally, central-line placements are common to gain jugular access and allow medications to be delivered. Finally, emerging uses include tumor ablation and surgical resection of organs (liver, lung, kidney, and so forth). In the case of tumor ablation, after ultrasound-guided targeting is achieved a biopsy-like needle may be employed to deliver energy (RF, microwave, cryo, and so forth) with the intent to kill tumor. In the case of an organ resection, intimate knowledge of subsurface anatomy during dissection, and display of a surgical device in relation to this anatomy, is key to gaining successful surgical margin while avoiding critical structures.

In each of these cases, the ultrasound-guidance typically offers a two dimensional image plane that is captured from the distal end of a patient-applied transducer. Of critical importance to the user for successful device placement is the ability to visualize and characterize the target, to choose the instrument angle and entry point to reach the target, and to see the surgical device and its motion toward the target. Today, the user images the target and uses a high level of skill to select the instrument angle and entry point. The user must then either move the ultrasound transducer to see the instrument path (thus losing site of the target) or assume the path is correct until the device enters the image plane. Of primary importance is the ability to choose the angle and entry point required to direct the device toward the ultrasound image plane (e.g., where the target is being imaged).

SUMMARY

This description may use the phrases "in an embodiment," "in embodiments," "in some embodiments," or "in other embodiments," which may each refer to one or more of the same or different embodiments in accordance with the present disclosure. For the purposes of this description, a phrase in the form "A/B" means A or B. For the purposes of the description, a phrase in the form "A and/or B" means "(A), (B), or (A and B)". For the purposes of this description, a phrase in the form "at least one of A, B, or C" means "(A), (B), (C), (A and B), (A and C), (B and C), or (A, B and C)".

As shown in the drawings and described throughout the following description, as is traditional when referring to relative positioning on a surgical device, the term "proximal" refers to the end of the apparatus that is closer to the user or generator, while the term "distal" refers to the end of the apparatus that is farther away from the user or generator. The term "user" refers to any medical professional (i.e., doctor, nurse, or the like) performing a medical procedure involving the use of aspects of the present disclosure described herein.

As used in this description, the term "surgical device" generally refers to a surgical tool that imparts electrosurgical energy to treat tissue. Surgical devices may include, but are not limited to, needles, probes, catheters, endoscopic instruments, laparoscopic instruments, vessel sealing devices, surgical staplers, etc. The term "electrosurgical energy" generally refers to any form of electromagnetic, optical, or acoustic energy.

Electromagnetic (EM) energy is generally classified by increasing frequency or decreasing wavelength into radio waves, microwaves, infrared, visible light, ultraviolet, X-rays and gamma-rays. As used herein, the term "microwave" generally refers to electromagnetic waves in the frequency range of 300 megahertz (MHz) ($3\times10^8$ cycles/second) to 300 gigahertz (GHz) ($3\times10^{11}$ cycles/second). As used herein, the term "RF" generally refers to electromagnetic waves having a lower frequency than microwaves. As used herein, the term "ultrasound" generally refers to cyclic sound pressure with a frequency greater than the upper limit of human hearing.

As used in this description, the term "ablation procedure" generally refers to any ablation procedure, such as microwave ablation, radio frequency (RF) ablation or microwave ablation-assisted resection. As it is used in this description, "energy applicator" generally refers to any device that can be used to transfer energy from a power generating source, such as a microwave or RF electrosurgical generator, to tissue.

As they are used in this description, the terms "power source" and "power supply" refer to any source (e.g., battery) of electrical power in a form that is suitable for operating electronic circuits. As it is used in this description, "transmission line" generally refers to any transmission medium that can be used for the propagation of signals from one point to another. As used in this description, the terms "switch" or "switches" generally refers to any electrical actuators, mechanical actuators, electro-mechanical actuators (rotatable actuators, pivotable actuators, toggle-like actuators, buttons, etc.), optical actuators, or any suitable device that generally fulfills the purpose of connecting and disconnecting electronic devices, or a component thereof, instruments, equipment, transmission line or connections and appurtenances thereto, or software.

As used in this description, "electronic device" generally refers to a device or object that utilizes the properties of electrons or ions moving in a vacuum, gas, or semiconductor. As it is used herein, "electronic circuitry" generally refers to the path of electron or ion movement, as well as the direction provided by the device or object to the electrons or ions. As it is used herein, "electrical circuit" or simply "circuit" generally refers to a combination of a number of electrical devices and conductors that when connected together, form a conducting path to fulfill a desired function. Any constituent part of an electrical circuit other than the interconnections may be referred to as a "circuit element" that may include analog and/or digital components.

The tem "generator" may refer to a device capable of providing energy. Such device may include a power source and an electrical circuit capable of modifying the energy outputted by the power source to output energy having a desired intensity, frequency, and/or waveform.

As it is used in this description, "user interface" generally refers to any visual, graphical, tactile, audible, sensory or other mechanism for providing information to and/or receiving information from a user or other entity. The term "user interface" as used herein may refer to an interface between a human user (or operator) and one or more devices to enable communication between the user and the device(s). Examples of user interfaces that may be employed in various embodiments of the present disclosure include, without limitation, switches, potentiometers, buttons, dials, sliders, a mouse, a pointing device, a keyboard, a keypad, joysticks, trackballs, display screens, various types of graphical user interfaces (GUIs), touch screens, microphones and other types of sensors or devices that may receive some form of human-generated stimulus and generate a signal in response thereto. As it is used herein, "computer" generally refers to anything that transforms information in a purposeful way.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" is any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other meta-languages. For the purposes of this definition, no distinction is made between languages which are interpreted, compiled, or use both compiled and interpreted approaches. For the purposes of this definition, no distinction is made between compiled and source versions of a program. Thus, reference to a program, where the programming language could exist in more than one state (such as source, compiled, object, or linked) is a reference to any and all such states. The definition also encompasses the actual instructions and the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

As it is used in this description, the phrase "treatment plan" refers to a selected ablation needle, energy level, and/or treatment duration to effect treatment of a target. The term "target" refers to a region of tissue slated for treatment, and may include, without limitation, tumors, fibroids, and other tissue that is to be ablated. The phrase "ablation zone" refers to the area and/or volume of tissue that will be ablated.

As it is used in this description, the phrase "computed tomography" (CT) or "computed axial tomography" (CAT) refer to a medical imaging method employing tomography created by computer processing. Digital geometry processing is used to generate a three-dimensional image of the inside of an object from a large series of two-dimensional X-ray images taken around a single axis of rotation.

As it is used in this description, the term magnetic resonance imaging (MRI), nuclear magnetic resonance imaging (NMRI), or magnetic resonance tomography (MRT) refer to a medical imaging technique used in radiology to visualize detailed internal structures. MRI makes use of the property of nuclear magnetic resonance (NMR) to image nuclei of atoms inside the body. An MRI machine uses a powerful magnetic field to align the magnetization of some atomic nuclei in the body, while using radio frequency fields to systematically alter the alignment of this magnetization. This causes the nuclei to produce a rotating magnetic field detectable by the scanner and this information is recorded to construct an image of the scanned area of the body.

As it is used in this description, the term "three-dimensional ultrasound" or "3D ultrasound" refers to medical ultrasound technique providing three dimensional images.

As it is used in this description, the phrase "digital imaging and communication in medicine" (DICOM) refers to a standard for handling, storing, printing, and transmitting information relating to medical imaging. It includes a file format definition and a network communications protocol. The communication protocol is an application protocol that uses TCP/IP to communicate between systems. DICOM files can be exchanged between two entities that are capable of receiving image and patient data in DICOM format.

Any of the herein described systems and methods may transfer data therebetween over a wired network, wireless network, point to point communication protocol, a DICOM communication protocol, a transmission line, a removable storage medium, and the like.

The systems described herein may utilize one or more sensors configured to detect one or more properties of tissue and/or the ambient environment. Such properties include, but are not limited to: tissue impedance, tissue type, tissue clarity, tissue compliance, temperature of the tissue or jaw members, water content in tissue, jaw opening angle, water motality in tissue, energy delivery, and jaw closure pressure.

In an aspect of the present disclosure, a planning and navigation system is provided. The planning system includes a memory configured to store a plurality of images and a first controller configured to render the plurality of images in three dimensions, automatically segment the plurality of images to demarcate a target area, and automatically determine a treatment plan based on the target area. The navigation system includes an ultrasound device having a fiducial pattern disposed thereon and configured to obtain an ultrasound image in a scan plane, a surgical device having a image capture device configured to capture a fiducial image of the fiducial pattern, and a second controller configured to receive the ultrasound image and the fiducial image, wherein the controller determines a position of the surgical device in relation to the scan plane based on the fiducial image. The planning and navigation system also includes a third controller configured to receive the rendered plurality of images, the target area, the treatment plan, the ultrasound image, and the position of the surgical device in relation to the scan plane and a display configured to display a first display having the rendered plurality of images, the target area, and the treatment plan and configured to display a second display having the ultrasound image, a virtual image of the surgical device based on the position of the surgical device in relation to the scan plane, and the treatment plan.

In the planning and navigation system the first display and the second display are displayed on a single screen and may be displayed simultaneously or a user can switch between the first display and the second display. Alternatively, the display may have two screens and the first display is displayed on a first screen and the second display is displayed on a second screen. The display may provide a graphical user interface.

The first controller performs a volumetric analysis to determine a treatment plan and an input means may be provided to adjust the treatment plan. The first controller may also segment at least one vessel and adjust the treatment plan based on the proximity of the vessel to the target or the first controller may segment at least one organ and adjust the treatment plan based on a position of the target in relation to the organ.

In the planning and navigation system, the fiducial pattern is affixed to a known location on the ultrasound device and the image capture device is affixed to a known location on the surgical device. The fiducial pattern has a plurality of markings of known characteristics and relative positions that reside within a known topology.

The second controller corresponds the fiducial image to a model image, estimates a camera pose, and transforms the surgical device to model coordinates. The second controller also corrects the fiducial image for lens distortion. Additionally, the second controller can recognize a topology within the fiducial marker where the topology references two or more independent unique identifiers located in a known position on a single pattern on a marker.

BRIEF DESCRIPTION OF THE DRAWINGS

The above and other aspects, features, and advantages of the present disclosure will become more apparent in light of the following detailed description when taken in conjunction with the accompanying drawings in which:

FIGS. 2A and 2B are schematic diagrams of an ablation needle according to an embodiment of the present disclosure;

FIG. 11A is a schematic diagram of a relationship between a vessel and a target according to another embodiment of the present disclosure;

FIG. 11B is a graphical representation of an alternate dosing curve according to another embodiment of the present disclosure;

FIGS. 12A-12C are schematic diagrams of a planning method according to another embodiment of the present disclosure;

FIGS. 16A and 16B depict an image taken by a camera and a corrected version of the image, respectively;

FIG. 17 is a flowchart depicting an algorithm for finding white circles according to an embodiment of the present disclosure;

FIGS. 20A-20D depict intermediate image results of the algorithm depicted in FIG. 19;

FIG. 24 is a schematic diagram of an integrated planning and navigation system according to yet another embodiment of the present disclosure;

FIGS. 25A and 25B are schematic diagrams of a navigation system suitable for use with the system of FIG. 24.

DETAILED DESCRIPTION

Figure 1:
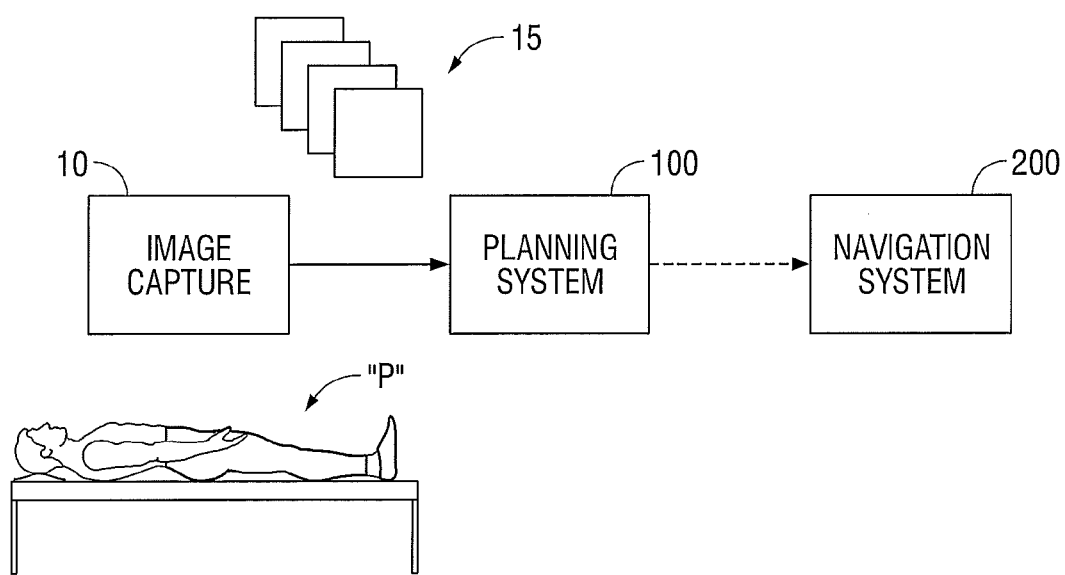
FIG. 1 is a system block diagram of a planning and navigation system according to an embodiment of the present disclosure.

Particular embodiments of the present disclosure are described hereinbelow with reference to the accompanying drawings; however, it is to be understood that the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

Turning to the figures, FIG. 1 depicts an overview of a planning and navigation system according to various embodiments of the present disclosure. As shown in FIG. 1, pre-operative images 15 of a patient "P" are captured via an image capture device 10. Image capture device 10 may include, but is not limited to, a MRI device, a CAT device, or an ultrasound device that obtains two-dimensional (2D) or three-dimensional (3D) images. Image capture device 10 stores pre-operative images 15 that are transferred to planning system 100. Pre-operative images 15 may be transferred to planning system 100 by uploading images 15 to a network, transmitting images 15 to planning system 100 via a wireless communication means, and/or storing images 15 on a removable memory that is inserted into planning system 100. In an embodiment of the present disclosure, pre-operative images 15 are stored in a DICOM format. In some embodiments, image capture device 10 and planning system 100 may be incorporated into a standalone unit.

Planning system 100, which is described in more detail below, receives the pre-operative images 15 and determines the size of a target. Based on the target size and a selected surgical device, planning system 100 determines settings that include an energy level and a treatment duration to effect treatment of the target.

Navigation system 200, which is described in more detail below, utilizes a fiducial pattern disposed on a medical imaging device (e.g., an ultrasound imaging device) to determine an intracorporeal position of an surgical device. The intracorporeal position of the surgical device is displayed on a display device in relation to an image obtained by the medical imaging device. Once the surgical device is positioned in the vicinity of the target, the user effects treatment of the target based on the treatment zone settings determined by the planning system.

In some embodiments, a user determines the treatment zone settings using planning system 100 and utilizes the treatment zone settings in effecting treatment using navigation system 200. In other embodiments, the planning system 100 transmits the treatment zone settings to navigation system 200 to automatically effect treatment of the target when the surgical device is in the vicinity of the target. Additionally, in some embodiments, planning system 100 and navigation system 200 are combined into a single standalone system. For instance, a single processor and a single user interface may be used for planning system 100 and navigation system 200, a single processor and multiple user interfaces may be used to for planning system 100 and navigation system 200, or multiple processors and a single user interface may be used for planning system 100 and navigation system 200.

FIG. 2A shows an example of a surgical device in accordance with an embodiment of the present disclosure. Specifically, FIG. 2A shows a side view of a variation on an ablation needle 60 with an electrical choke 72 and FIG. 2B shows a cross-section side view 2B-2B from FIG. 2A. Ablation needle 60 shows radiating portion 62 electrically attached via feedline (or shaft) 64 to a proximally located coupler 66. Radiating portion 62 is shown with sealant layer 68 coated over section 62. Electrical choke 72 is shown partially disposed over a distal section of feedline 64 to form electrical choke portion 70, which is located proximally of radiating portion 62.

To improve the energy focus of the ablation needle 60, the electrical choke 72 is used to contain field propagation or radiation pattern to the distal end of the ablation needle 60. Generally, the choke 72 is disposed on the ablation needle 60 proximally of the radiating section. The choke 72 is placed over a dielectric material that is disposed over the ablation needle 60. The choke 72 is a conductive layer that may be covered by a tubing or coating to force the conductive layer to conform to the underlying ablation needle 60, thereby forming an electrical connection (or short) more distally and closer to the radiating portion 62. The electrical connection between the choke 72 and the underlying ablation needle 60 may also be achieved by other connection methods such as soldering, welding, brazing, crimping, use of conductive adhesives, etc. Ablation needle 60 is electrically coupled to a generator that provides ablation needle 60 with electrosurgical energy.

Figure 3:
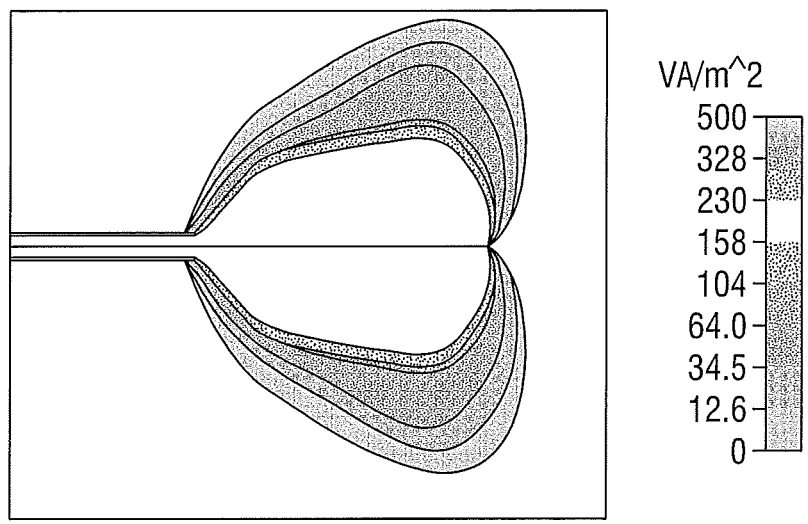
FIG. 3 is a schematic diagram of a radiation pattern of the ablation needle of FIGS. 2A and 2B.

FIG. 3 is a cross-sectional view of an embodiment of the ablation needle 60 shown with a diagrammatic representation of an emitted radiation pattern in accordance with the present disclosure.

Figure 4:
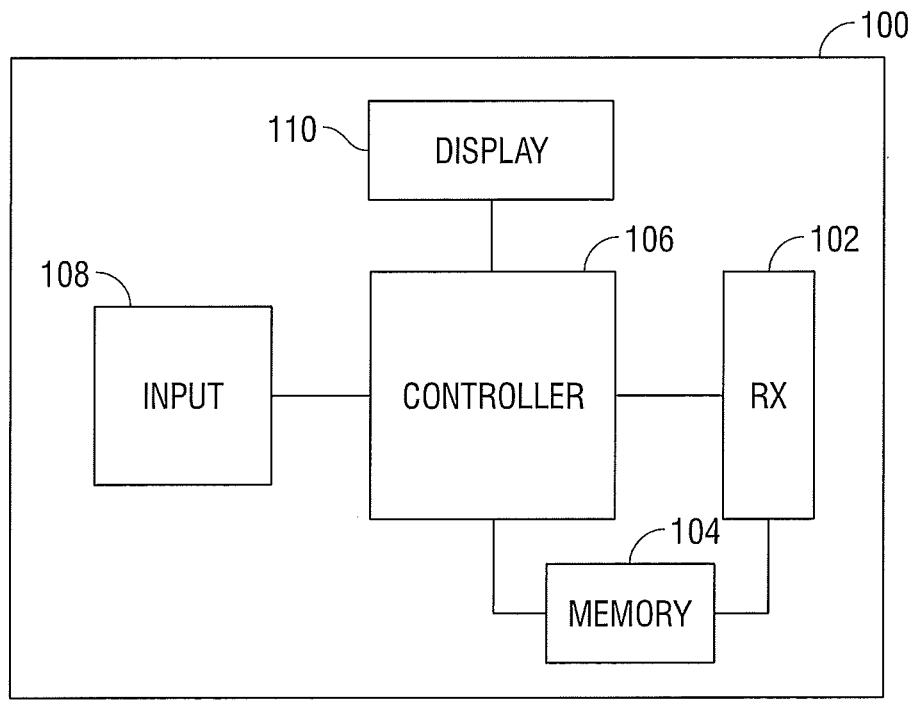
FIG. 4 is a schematic diagram of a planning system according to an embodiment of the present disclosure.

FIGS. 4 to 12C describe the operation of planning system 100 in accordance with various embodiments of the present disclosure. Turning to FIG. 4, planning system 100 includes a receiver 102, memory 104, controller 106, input device 108 (e.g., mouse, keyboard, touchpad, touchscreen, etc.), and a display 110. During operation of the planning system 100, receiver 102 receives pre-operative images 15 in DICOM format and stores the images in memory 104. Controller 106 then processes images 15, which is described in more detail below, and displays the processed images on display 110. Using input device 108, a user can navigate through the images 15, select one of the images from images 15, select a seed point on the selected image, select an ablation needle, adjust the energy level, and adjust the treatment duration. The inputs provided by input device 108 are displayed on display 110.

Figure 5:
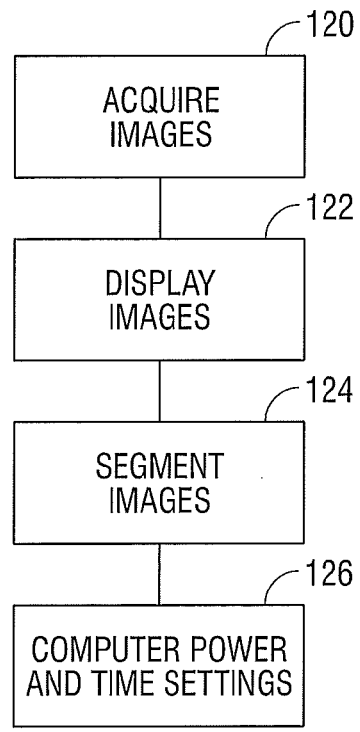
FIG. 5 is a flowchart depicting overall operation of the planning system according to an embodiment of the present disclosure.
Figure 6:
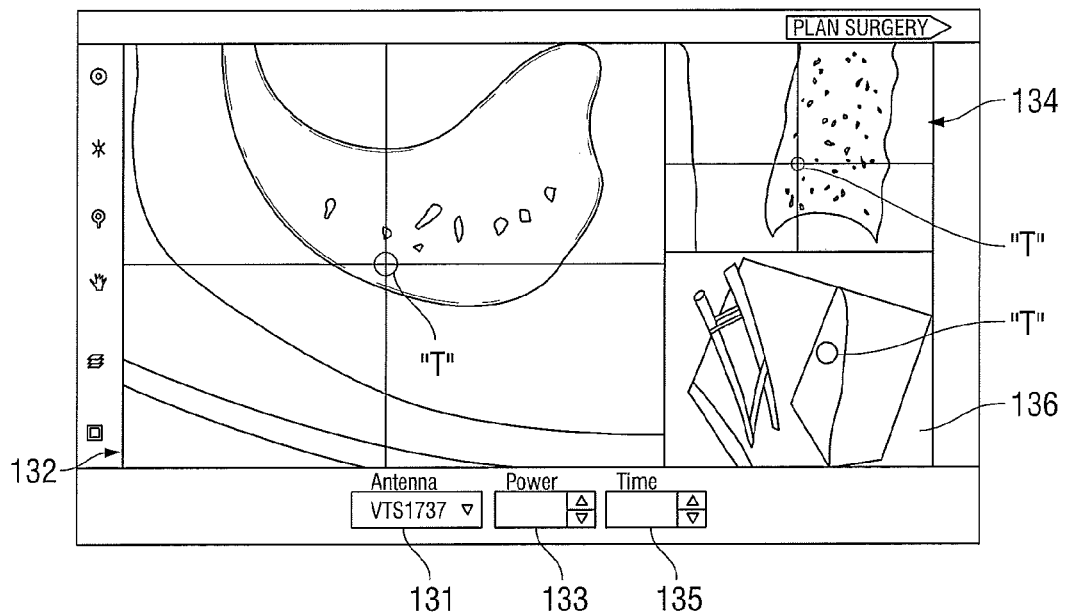
FIGS. 6 and 7 are schematic diagrams of graphical user interfaces used in the planning system in accordance with an embodiment of the present disclosure.

FIG. 5 depicts a general overview of an algorithm used by planning system 100 to determine a treatment plan. As shown in FIG. 5, in step 120, images in a DICOM format are acquired via a wireless connection, a network, or by downloading the images from a removable storage medium and stored in memory 104. Controller 106 then performs an automatic three dimensional (3D) rendering of the images 15 and displays a 3D rendered image (as shown in FIG. 6) in step 122. In step 124, image segmentation is performed to demarcate specific areas of interest and calculate volumetrics of the areas of interest. As described below, segmentation can be user driven or automatic. In step 126, the controller performs an inverse planning operation, which will also be described in more detail below, to determine a treatment algorithm to treat the areas of interest. The treatment algorithm may include selection of a surgical device, energy level, and/or duration of treatment. Alternatively, a user can select the surgical device, energy level, and/or duration of treatment to meet the intentions of a treating physician that would include a "margin value" in order to treat the target and a margin of the surrounding tissue.

Figure 7:
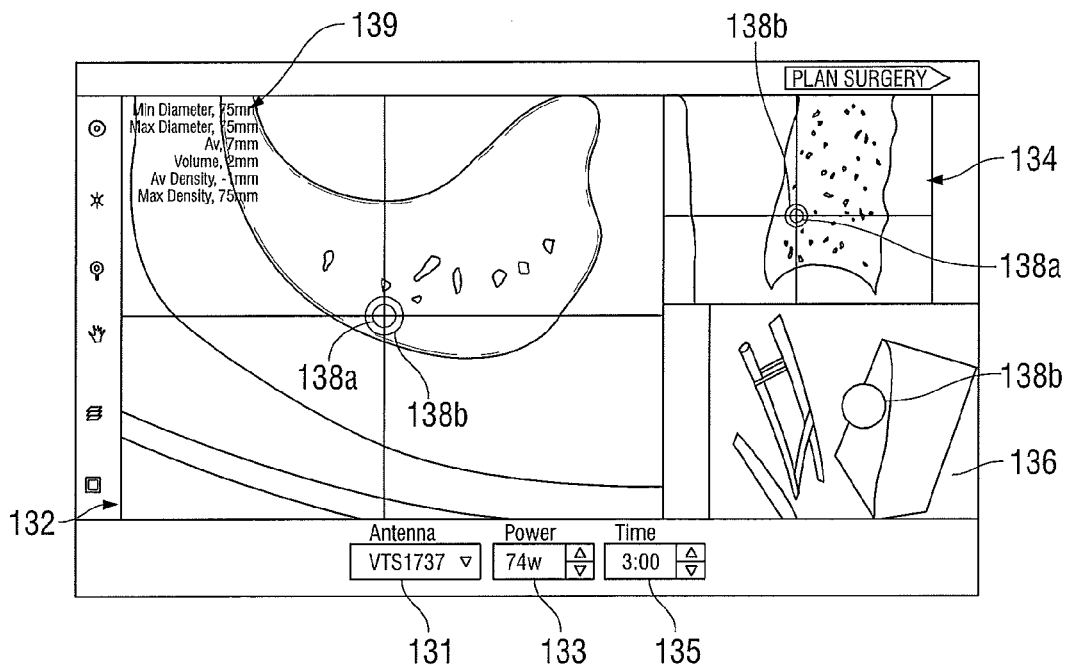

FIGS. 6 and 7 depict graphical user interfaces (GUIs) that may be displayed on display 110. As shown in FIGS. 6 and 7, each GUI is divided into a number of regions (e.g., regions 132, 134, and 136) for displaying the rendered DICOM images. For example, region 132 shows an image of patient "P" along a transverse cross-section and region 134 shows an image of patient "P" along a coronal cross-section. Region 136 depicts a 3D rendering of patient "P". In other embodiments, a sagittal cross-section may also be displayed on the GUI. The GUI allows a user to select different ablation needles in drop down menu 131. The GUI also allows a user to adjust the power and time settings in regions 133 and 135, respectively. Additionally, the GUI has a number of additional tools in region 137 that include, but are not limited to, a planning tool that initiates the selection of a seed point, a contrast tool, a zoom tool, a drag tool, a scroll tool for scrolling through DICOM images, and a 3D Render tool for displaying the volume rendering of the DICOM dataset.

Figure 8:
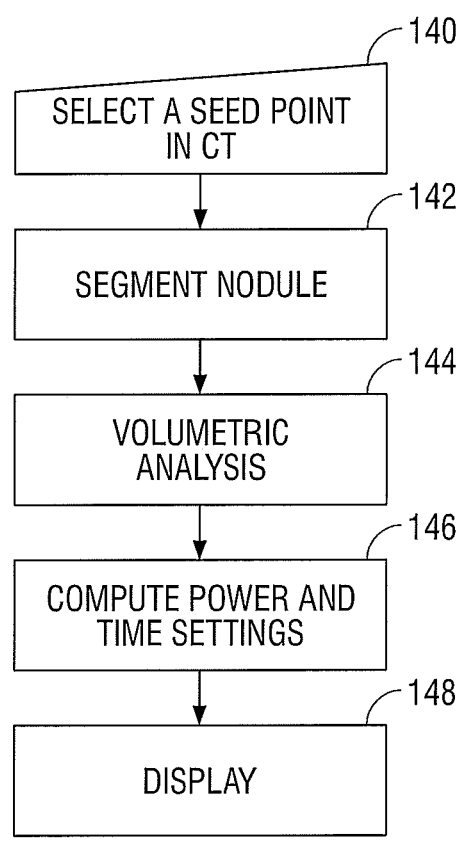
FIG. 8 is a flowchart depicting an algorithm for image segmentation and inverse planning according to an embodiment of the present disclosure.

The flowchart of FIG. 8 depicts the basic algorithm for performing the image segmentation step 124 and the inverse planning step 126. As shown in FIG. 8, a user selects a seed point in step 140 (see FIG. 6 where a cross hair is centered on the target "T" in regions 132 and 134). After the seed point is manually selected, planning system 100 segments a nodule to demarcate a volume of interest in step 142. In other embodiments, the seed point may be automatically detected based on the intensity values of the pixels.

Figure 9:
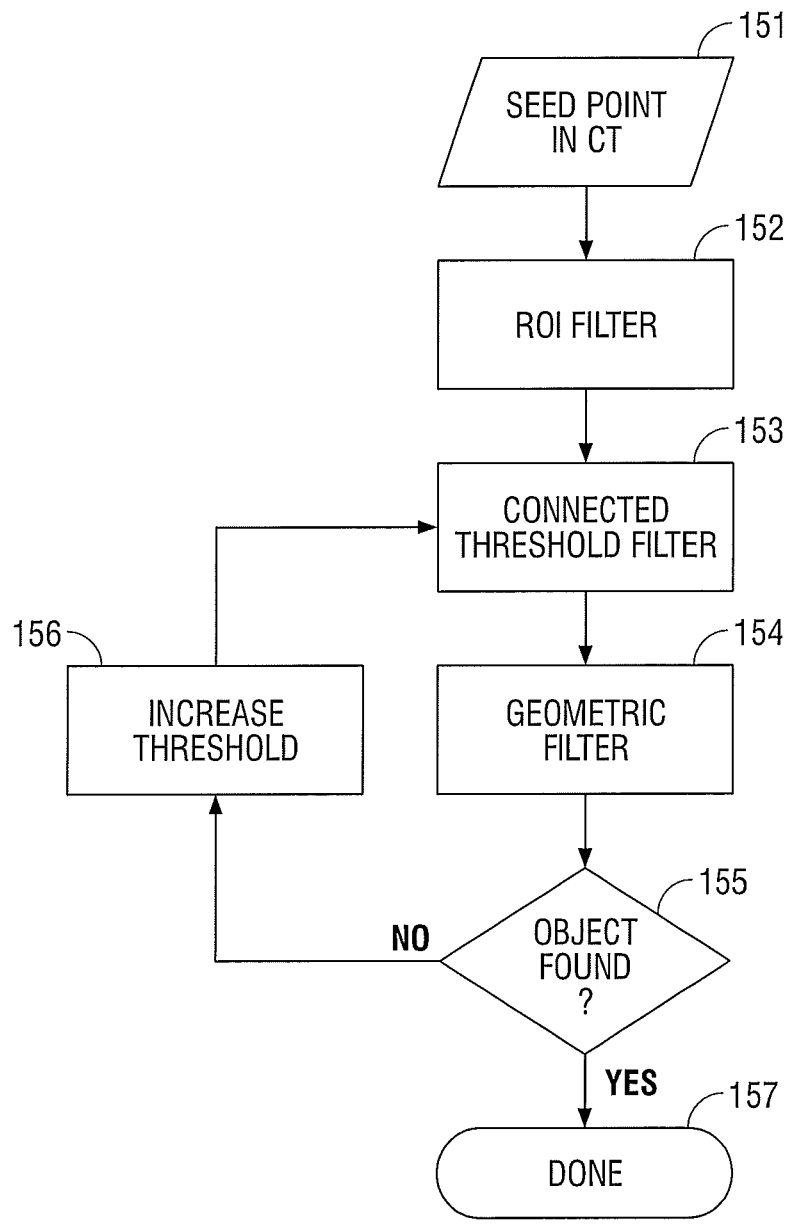
FIG. 9 is a flowchart depicting an algorithm for segmenting a nodule according to an embodiment of the present disclosure.

FIG. 9 depicts a flowchart of an algorithm used to segment a nodule. As shown in FIG. 9, once a seed point is identified in step 151, the algorithm creates a Region of Interest (ROI) in step 152. For example, the ROI may encompass a volume of 4 cm$^3$. In step 153, a connected threshold filter applies a threshold and finds all the pixels connected to the seed point in the DICOM images stored in memory 104. For example, the threshold values may start at −400 Houndsfields Units (HU) and end at 100 HU when segmenting lung nodules.

In step 154, controller 106 applies a geometric filter to compute the size and shape of an object. The geometric filter enables the measurement of geometric features of all objects in a labeled volume. This labeled volume can represent, for instance, a medical image segmented into different anatomical structures. The measurement of various geometric features of these objects can provide additional insight into the image.

The algorithm determines if a predetermined shape is detected in step 155. If a predetermined shape is not detected, the algorithm proceeds to step 156 where the threshold is increased by a predetermined value. The algorithm repeats steps 153 to 155 until a predetermined object is detected.

Once a predetermined object is detected, the algorithm ends in step 157 and the planning system 100 proceeds to step 144 to perform volumetric analysis. During the volumetric analysis, the following properties of the spherical object may be calculated by controller 106: minimum diameter; maximum diameter; average diameter; volume; sphericity; minimum density; maximum density; and average density. The calculated properties may be displayed on display 110 as shown in region 139 of FIG. 7. The volumetric analysis may use a geometric filter to determine a minimum diameter, a maximum diameter, volume, elongation, surface area, and/or sphericity. An image intensity statistics filter may also be used in conjunction with the geometric filter in step 144. The image intensity statistics filter calculates a minimum density, maximum density, and average density.

Figure 10A:
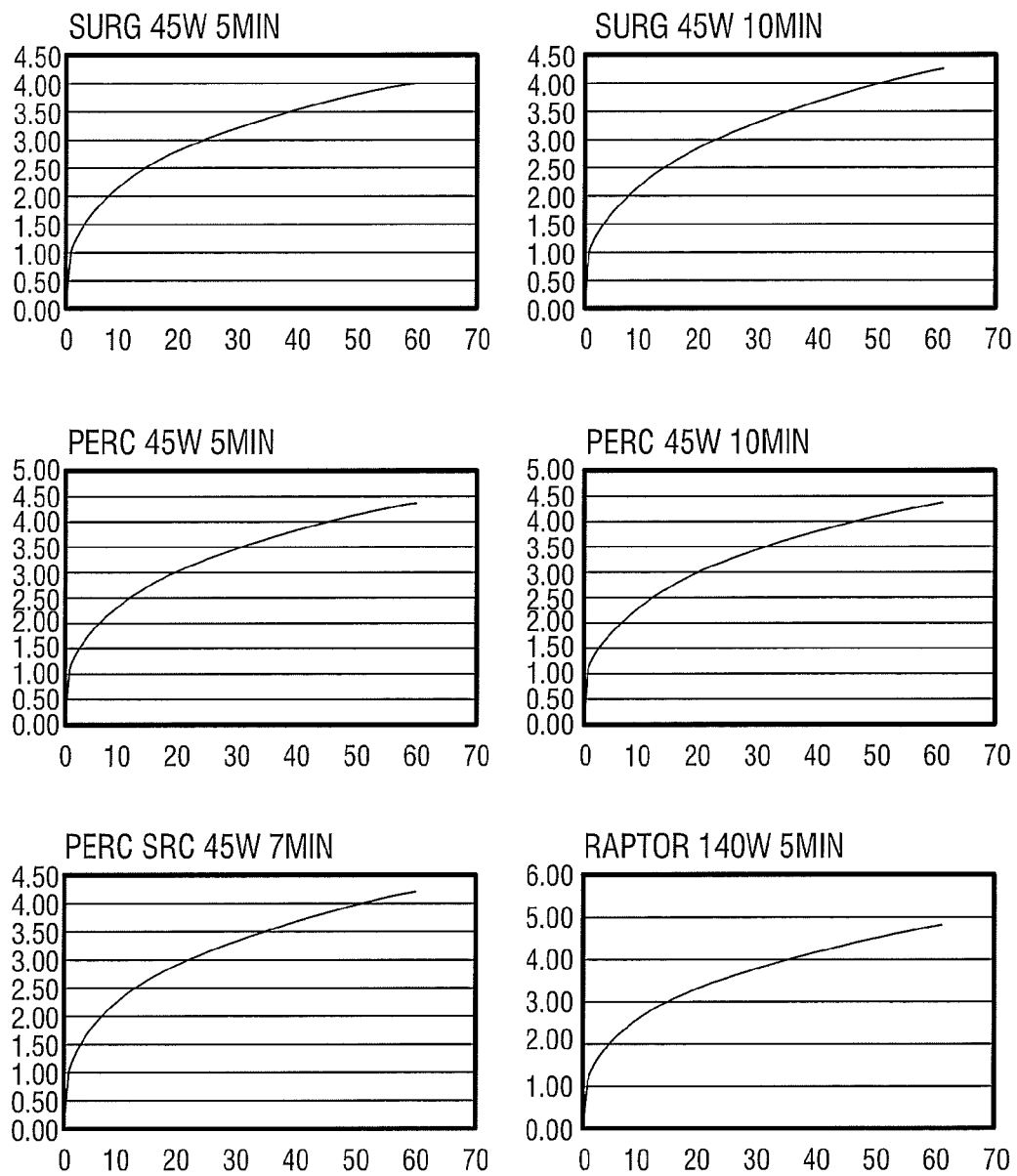
FIGS. 10A-10B are graphical representations of relationships between ablation zones and energy delivery.
Figure 10B:
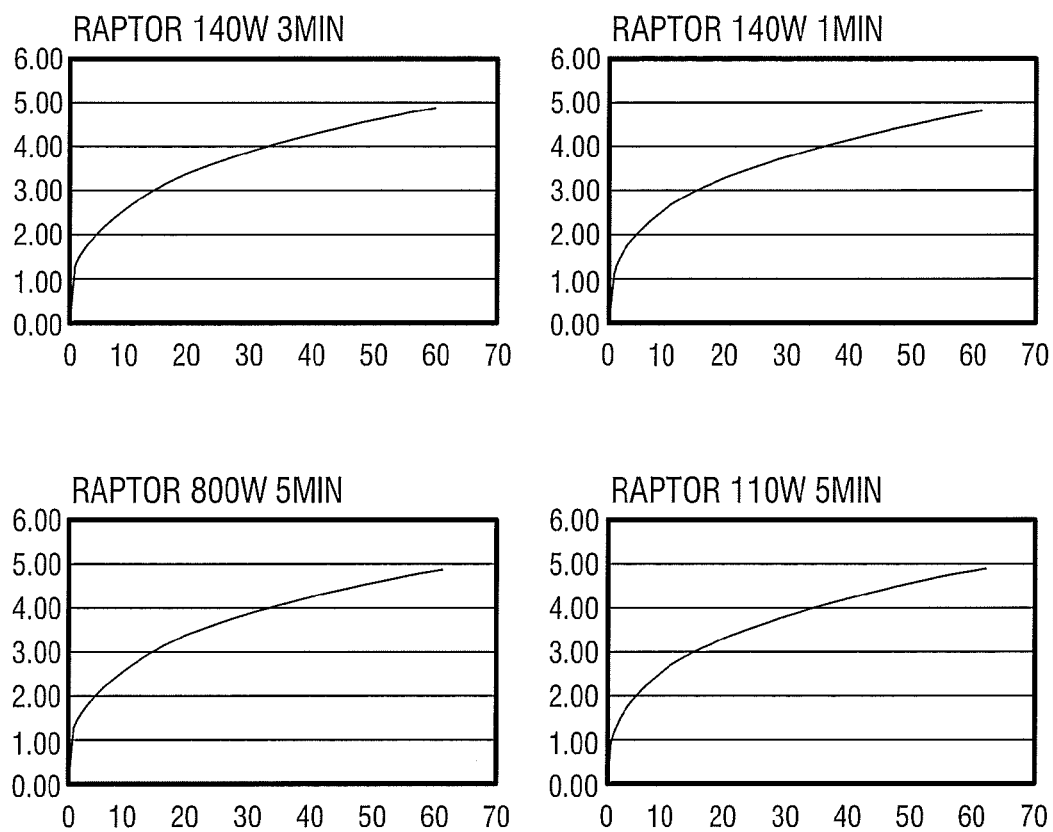

In step 146, power and time settings are calculated for a demarcated target. FIG. 10 depicts various graphs of the relation ship between energy deposited into tissue and the resulting ablation zone for a given time period. This relationship allows for inverse planning by considering the dimension and characteristics of a target tissue (i.e., tumors, fibroids, etc.) and the energy dose/antenna design of a specific ablation needle. Table 1 below shows an example of a relationship between ablation volume, power, and time for an ablation needle.

TABLE 1

| Ablation Volume (cm$^3$) | Power (W) | Time (s) |
|---|---|---|
| 6 | 140 | 1 |
| 22 | 140 | 3 |
| 41 | 140 | 5 |
| 31 | 110 | 5 |
| 23 | 80 | 5 |

Using the values in Table 1, a linear equation can be derived from the table to compute optimal power and time settings. For example, using a linear regression analysis, Table 1 provides the following equation:

$$Volume = 0.292381*Power + 8.685714*Time - 44.0762 \qquad (1)$$

which can be written as $$Power = (Volume - 8.685714*Time + 44.0762)/0.292381. \qquad (2)$$

The desired volume can be calculated using the maximum diameter from the volumetric analysis plus a 1 centimeter margin as follows:

$$\text{DesiredVolume} = 4/3 * pi * \text{DesiredRadius}^3 \quad (3)$$

where the desired radius is calculated as follows:

$$\text{DesiredRadius} = \text{MaximumNoduleDiameter}/2 + \text{Margin}. \quad (4)$$

Substituting the desired volume into equation (1) or (2) leaves two unknowns, power and time. Using equation (2) controller 106 can solve for power by substituting values for time. Controller 106 chooses the smallest value for time that maintains power below 70 W, or some other predetermined value, so that the user can perform the procedure as quickly as possible while keeping power in a safe range.

Once the power and time are calculated 146, the power and time are displayed on display 110 as shown in FIG. 7 (see 133 and 135). A user can adjust the calculated power and/or time using controls 133 and 135, respectively, to adjust the treatment zone 138*a* and/or margin 138*b*.

Memory 104 and/or controller 106 may store a number of equations that correspond to different surgical devices. When a user selects a different surgical devices in drop down menu 131, controller 106 can perform the same analysis described above to determine the smallest value for time that keeps the power below 70 W or some other predetermined value.

Although the above described procedure describes the use of a single seed point to determine a predetermined object, some targets may have an irregular shape that can not be treated by the predetermined treatment zone without causing damage to other tissue. In such instances, multiple seed points may be used to create an irregular shaped treatment plan using a single surgical device that is repositioned in a number of places or multiple surgical devices that may be used concurrently to treat an irregularly shaped region.

In other embodiments, memory 104 and/or controller 106 may store a catalog of surgical devices and treatment zone performance, which includes power, time, number of instruments, and spacing of instruments required to achieve treatment zones ex vivo or in vivo. Based on the results of the image segmentation and volumetric analysis, the controller may automatically select device types, numbers of devices, spacing of multiple devices, and/or power and time settings for each device to treat the ROI. Alternatively, a user can manually select device types, numbers of devices, spacing of multiple devices, power and/or time settings for each device to treat the ROI using the GUI to generate a treatment plan.

In another embodiment according to the present disclosure, planning system 100 may also segment organs and other vital structures in addition to targets. Segmentation of organs and other structures, such as vessels, are used to provide a more advanced treatment plan. As described above with regard to FIG. 10, treatment zones correlate to energy delivery in a regular fashion. Further, it is known that vessels greater than three (3) millimeters may negatively affect treatment zone formation. Segmentation of a vessel would allow the interaction between the vessels and the target to be estimated, including the vessel diameter (D1) and distance (D2) (see FIG. 11A) between the vessel and a proposed target. This interaction may be estimated manually by a user or automatically by controller 106. Using the vessel diameter D1 and the distance D2, planning system 100 may automatically suggest an alternate dose curve to be used for treatment purposes as shown in FIG. 11B. Alternatively, controller 106 may provide a recommendation to the user via display 110 to move the treatment zone. Additionally, a different treatment zone projection could be displayed on display 110. Further, in the compute power and time settings step 146 of FIG. 8, the controller could leverage different curves depending on the vessel's diameter and distance to the target area.

FIGS. 12A-12C depict an advanced treatment planning using organ segmentation. Segmentation of an organ allows for at least two advantages in planning a course of treatment. In a first instance, minimally invasive treatments are often chosen to be organ sparing. By segmenting the organ, controller 106 can calculate the organ volume 160 and subtract the determined ablation zone 162 to determine the volume of organ being spared 164 as shown in FIG. 12A. If controller 106 determines that volume of organ being spared is too low, controller 106 may alert a user that an alternate treatment plan is needed or it may suggest an alternate treatment plan.

FIGS. 12B and 12C depict a treatment plan for a target "T" located on the surface of an organ. Conventionally, treatment near an organ surface is often avoided or additional techniques may be required to separate the organ from other organs before treatment can be performed. In another embodiment in accordance with the present disclosure, after the organ is segmented, the position of a target "T" can also be determined. If the treatment zone 162 in the treatment plan projects outside the surface of the organ and the target "T" is located on the surface, controller 106 may alert the user that treatment zone 162 may affect other organs and/or structures in the vicinity of the target "T" and that the treatment plan needs to be altered. In another embodiment, controller 106 may automatically make recommendations to the user indicating the surgical device, energy level, duration of treatment. Controller 106 may also suggest a smaller treatment zone 162 as shown in FIG. 12B or it may suggest moving the treatment zone 162 as shown in FIG. 12C.

In other embodiments, after targets, tissues, organs, and other structures are segmented, known tissue properties can be attributed to these structures. Such tissue properties include, but are not limited to, electrical conductivity and permittivity across frequency, thermal conductivity, thermal convection coefficients, and so forth. The planning algorithm of FIG. 8 may use the tissue properties attributed to the segmented tumors, tissues, organs, and other structures to solve the Pennes bioheat equation in order to calculate a dose required to ablate a selected target. Keys to successful implementation of this more comprehensive solution using the bioheat equation include: utilizing known tissue properties at steady-state to predict an initial spatial temperature profile, utilizing tissue properties as temperature rises to adjust spatial properties in accordance with temperature elevation, and utilizing tissue properties at liquid-gas phase transition.

Figure 13:
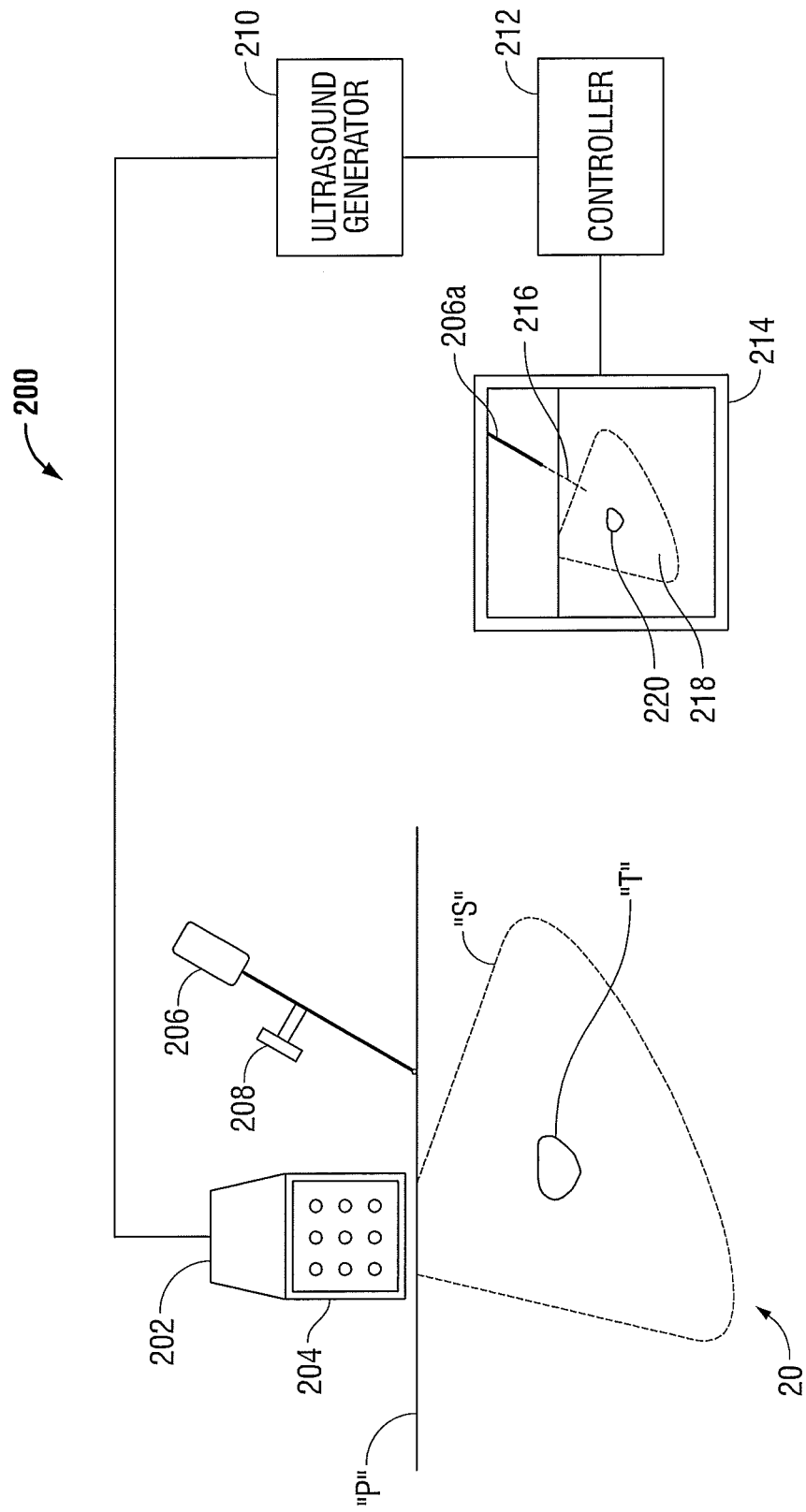
FIG. 13 is a schematic diagram of a navigation system according to an embodiment of the present disclosure.

Turning to FIG. 13, a navigation system in accordance with an embodiment of the present disclosure is shown generally as 200. Generally, navigation system 200 incorporates a reference patch or fiducial patch 204 that is affixed to an ultrasound transducer 202. Fiducial patch 204 may be printed on ultrasound transducer 202, attached to ultrasound transducer 202 via an adhesive, or removably coupled to ultrasound transducer 202. In some embodiments, the fiducial patch is disposed on a support structure that is configured to be removably affixed, e.g., "clipped onto", the housing of an ultrasound transducer. Ultrasound transducer 202 is coupled to an ultrasound generator 210 that generates acoustic waves. Ultrasound transducer 202 and ultrasound generator 210 may be incorporated into a standalone unit. Ultrasound transducer 202 emits the acoustic waves toward patient "P". The acoustic waves reflect off various structures in patient "P" and are received by ultrasound transducer 202. Ultrasound transducer 202 transmits the reflected acoustic waves to an ultrasound generator 210 that converts the reflected acoustic waves into a two dimensional (2D) image in real time. The 2D image is transmitted to a controller 212. Controller 212 processes the 2D image and displays the 2D image as image 218 including target 220 on display 214. Image 218 is a real time representation of scan plane "S" which may include target "T".

The navigation system also incorporates a camera 208 affixed to an surgical device 206. The camera 208 captures an image of fiducial patch 204 in real time in order to determine the position of the surgical device 206 in relation to the scan plane "S". In particular, fiducial patch 204 has a defined spatial relationship to scan plane "S". This defined spatial relationship is stored in controller 212. Camera 208 also has a known spatial relationship to surgical device 206 that is stored in controller 212. In order to determine the spatial relationship between surgical device 206 and scan plane "S", camera 208 captures an image of fiducial patch 204 and transmits the image to controller 212. Using the image of the fiducial patch 204, controller 212 can calculate the spatial relationship between the surgical device 206 and the scan plane "S".

After controller 212 determines the spatial relationship between the surgical device 206 and scan plane "S", controller 212 displays that relationship on display 214. As shown in FIG. 13, display 214 includes an image 218 of scan plane "S" including a target image 220 of target "T". Additionally, controller 212 superimposes a virtual image 206a of surgical device 206 in relation to image 218 to indicate the position of the surgical device 206 in relation to scan plane "S". Based on the angle and position of the ablation needle 206, controller 212 can calculate a trajectory of the surgical device 206 and display the calculated trajectory shown generally as 216. In some embodiments, a crosshair or target may be superimposed on image 218 to indicate where the surgical device 206 will intersect the scan plane "S". In other embodiments, the calculated trajectory 216 may be shown in red or green to indicate the navigation status. For instance, if surgical device 206 is on a path that will intersect target "T", calculated trajectory 216 will be shown in green. If surgical device 206 is not on a path that will intersect target "T", calculated trajectory 216 will be shown in red.

Figure 14A:
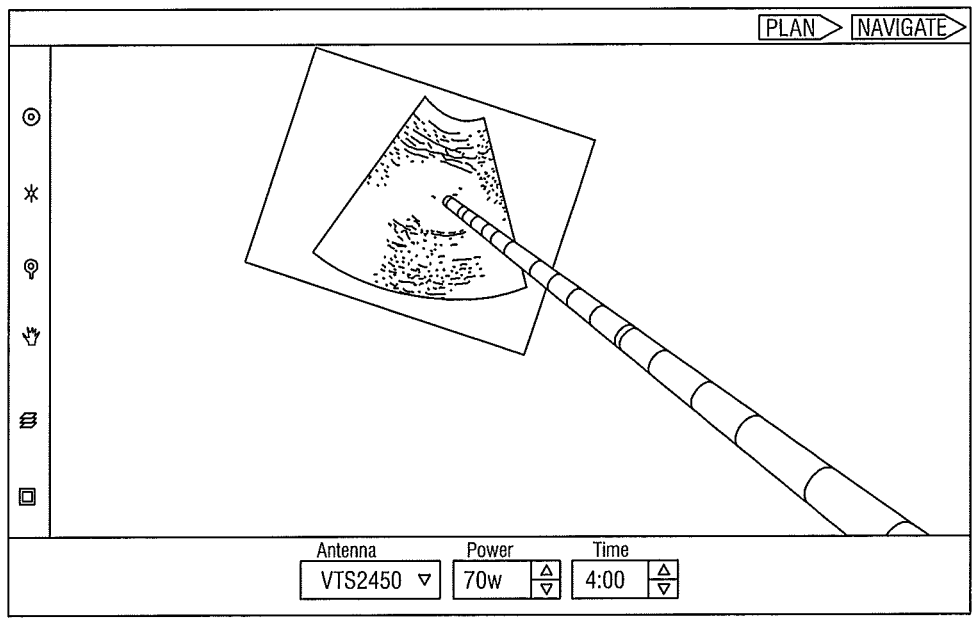
FIGS. 14A and 14B are schematic diagrams of graphical user interfaces used in the navigation system of FIG. 13.
Figure 14B:
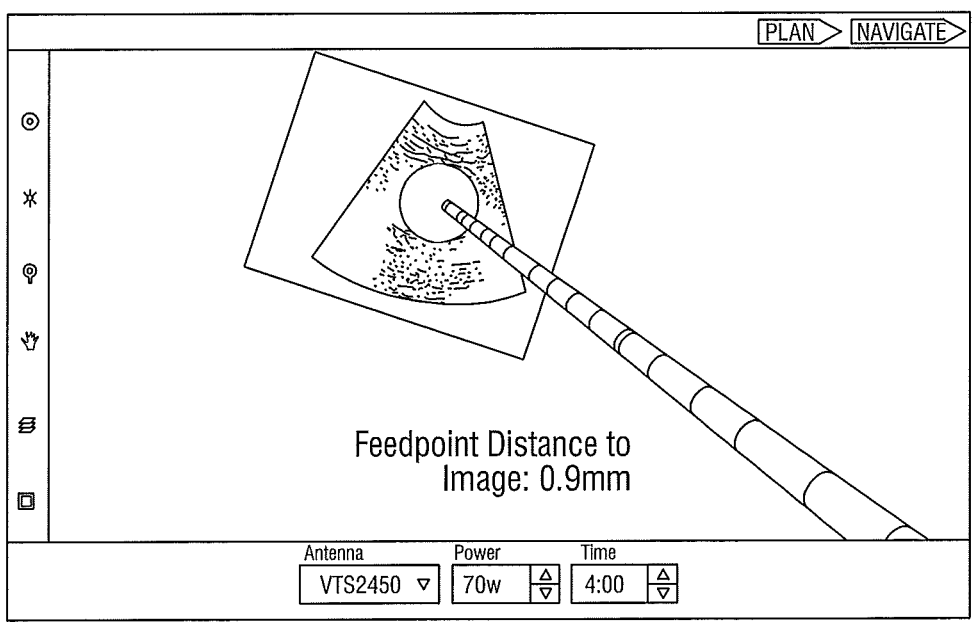

Controller 212 can also be controlled by a user to input the surgical device type, energy level, and treatment duration. The surgical device type, energy level, and treatment duration can be displayed on display 214 as shown in FIG. 14A. When surgical device 206 intersects target "T", a virtual ablation zone 222 is projected onto image 218 as shown in FIG. 14B. The energy level and treatment duration can then be adjusted by a user and the controller 212 will adjust the virtual ablation zone 222 to reflect the changes in the energy level and treatment duration.

The fiducial tracking system is described hereinbelow with reference to FIGS. 15-22. In the fiducial tracking system, controller 212 receives a fiducial image from camera 208. Controller 212 also includes camera calibration and distortion coefficients for camera 208, fiducial system models, and camera-antenna calibration data previously stored thereon. In other embodiments, camera calibration and distortion coefficients for camera 208, fiducial system models, and camera-antenna calibration data can be entered into controller 212 during a navigation procedure. Based on the fiducial image, camera calibration and distortion coefficients for camera 208, fiducial system models, and camera-antenna calibration data, controller 212 can output the position of ablation needle 206 to display 214 as well as diagnostic frame rate, residual error, and tracking status. In some embodiments, the distance between the camera 208 and the fiducial patch 204 may be in the range of about 5 to about 20 centimeters. In some embodiments, the distance between camera 208 and fiducial patch 204 may be in the range of about 1 to about 100 centimeters.

Figure 15:
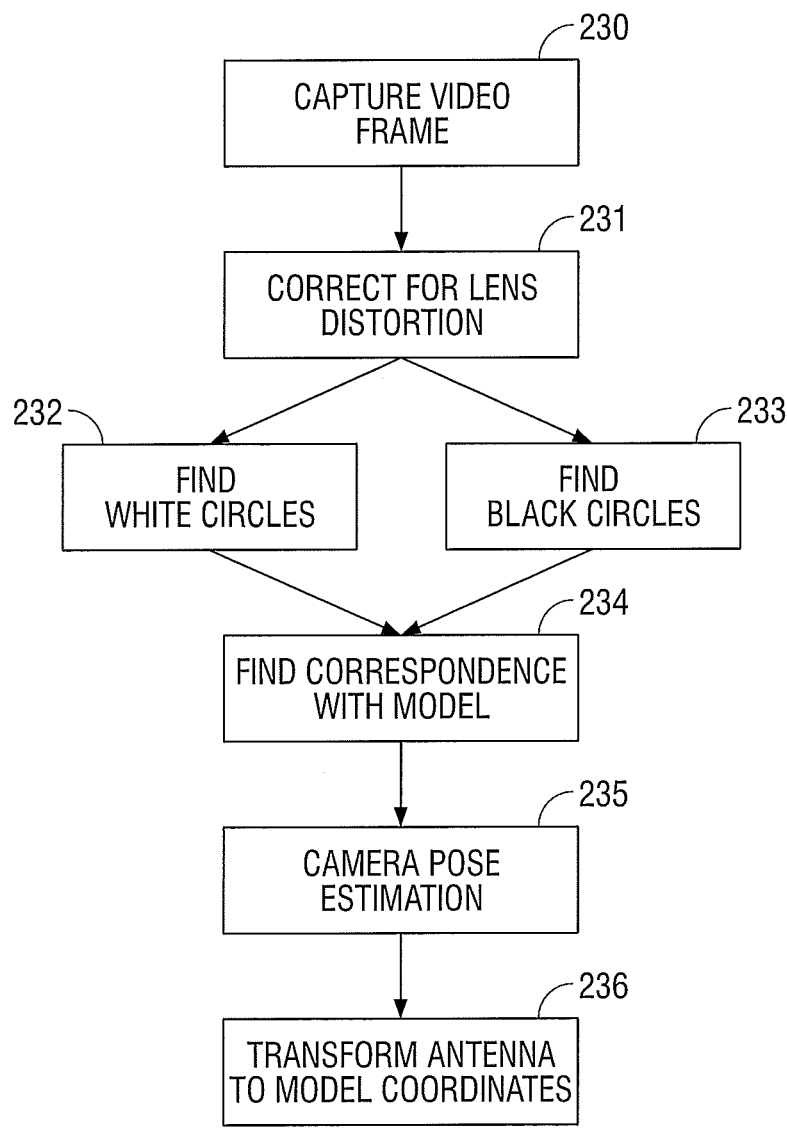
FIG. 15 is a flowchart depicting a fiducial tracking algorithm according to an embodiment of the present disclosure.

FIG. 15 shows a basic flowchart for the fiducial tracking algorithm employed by controller 212. As shown in FIG. 15, an image frame is captured in step 230. In step 231, controller 212 corrects for lens distortion using the camera calibration and distortion coefficients. Images captured by camera 208 may exhibit lens distortion as shown in FIG. 16A. Thus, before an image can be used for further calculations, the image needs to be corrected for the distortion. Before camera 208 is used during a navigation procedure, camera 208 is used to take multiple images of a checkerboard pattern at various angles. The multiple images and various angles are used to create a camera matrix and distortion coefficients. Controller 212 then uses the camera matrix and distortion coefficients to correct for lens distortion.

In step 232, controller 212 finds the white circles in the image frame using the algorithm of FIG. 17. As shown in FIG. 17, the image frame received in step 241 (FIG. 18A) is thresholded in step 243 using a dynamic threshold (see FIG. 18B). When using a dynamic threshold, after each valid frame, the dynamic threshold algorithm computes a new threshold for the next frame using the circles that were found in the valid frame. Using the circles that were found in the valid frame, controller 212 calculates a new threshold based on equation (5) below:

$$\text{threshold} = (\text{black circle intensity}_{average} + \text{white circle intensity}_{average})/2 \quad (5)$$

A predetermined threshold may be used to capture the initial valid frame which is then used to calculate a new threshold.

Alternatively, controller 212 may scan for an initial threshold by testing a range of threshold values until a threshold value is found that results in a valid frame. Once an initial threshold is found, controller 212 would use equation (5) for dynamic thresholding based on the valid frame.

In other embodiments, a fixed threshold may be used. The fixed threshold may be a predetermined number stored in controller 212 or it may be determined by testing the range of threshold values until a threshold value is found that results in a valid frame.

Figure 18A:
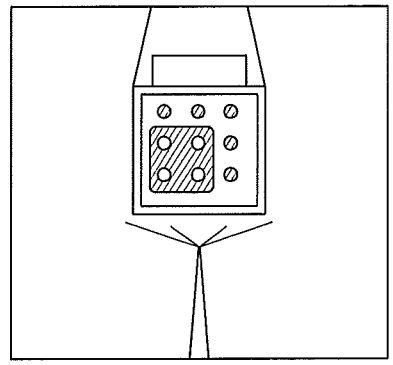
FIGS. 18A-18C depict intermediate image results of the algorithm depicted in FIG. 17.
Figure 18B:
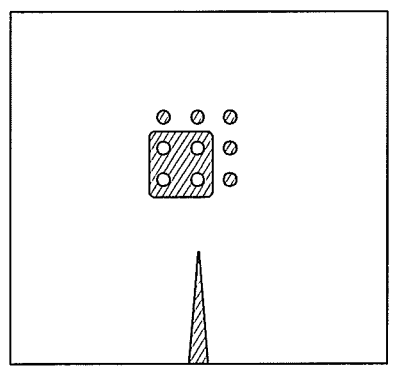
Figure 18C:
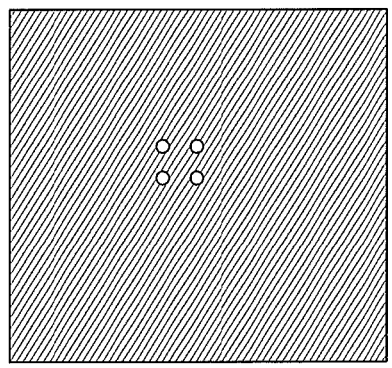

After a threshold and automatic gain control is applied to the image, a connected component analysis is performed in step 244 to find all the objects in the thresholded image. A geometric filter is applied to the results of the connected component analysis and the image frame in step 245. The geometric filter computes the size and shape of the objects and keeps only those objects that are circular and about the right size as shown in FIG. 18C. Weighted centroids are computed and stored for all the circular objects.

Figure 19:
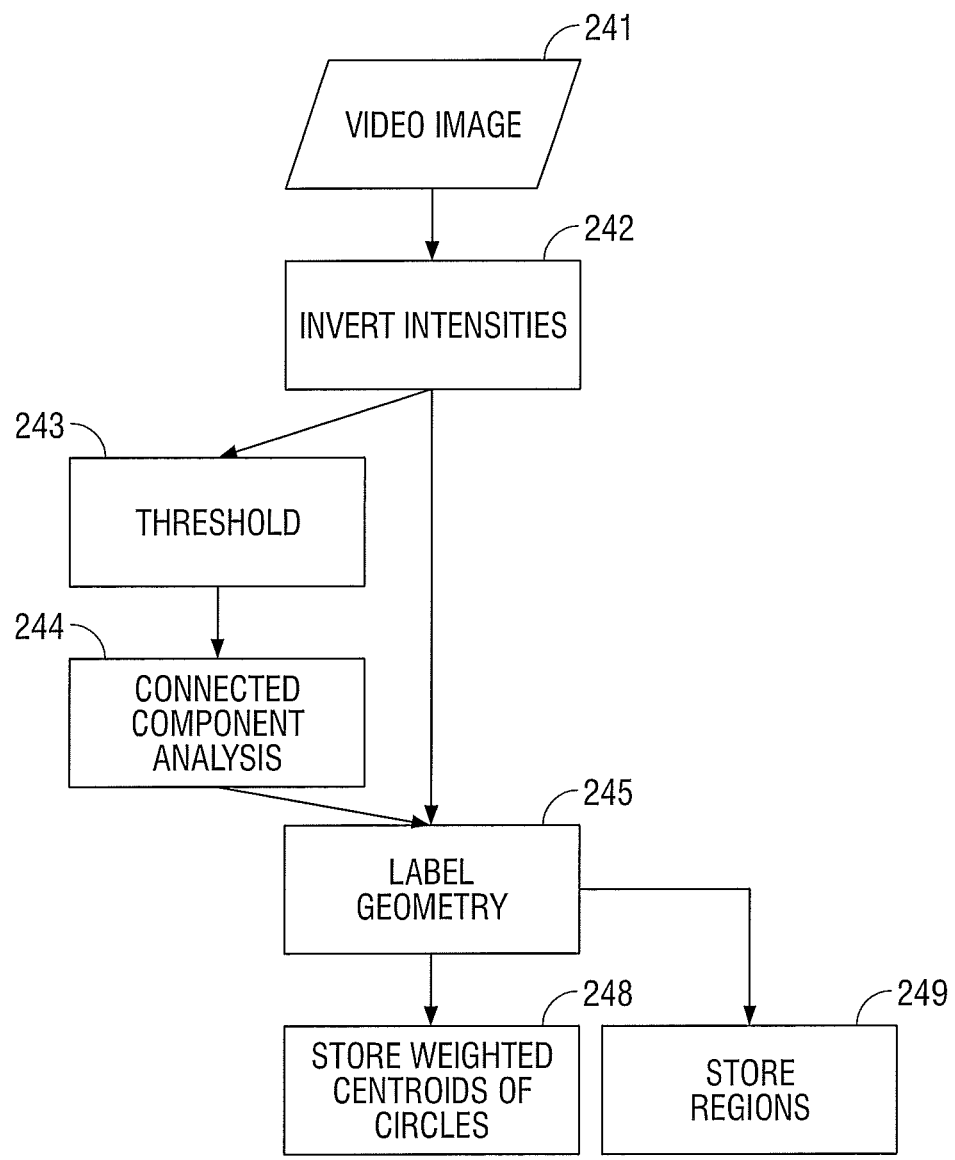
FIG. 19 is a flowchart depicting an algorithm for finding black circles and black regions according to an embodiment of the present disclosure.

Turning back to FIG. 15, in addition to finding the white circles in step 232, controller 212 also finds the black circles in step 233 using the algorithm depicted in FIG. 19. The algorithm for finding the black circles is similar to the algorithm shown in FIG. 17 for finding the white circles. In order to find the black circles, after an image frame is received in step 241 (see FIG. 20A), controller 212 inverts the intensities of the image frame in step 242 as shown in FIG. 20B. Then, as described above with regard to FIG. 17, the image is thresholded as shown in FIG. 20C and the connected component analysis is performed and geometric filter is applied to obtain the image shown in FIG. 20D. The weighted centroids are computed and stored for all the black circles in step 248. Further, in step 245, controller 212 applies a geometric filter to determine the black regions in addition to the black circles in the image frame. Controller 212 stores the determined black regions in step 249.

Figure 21A:
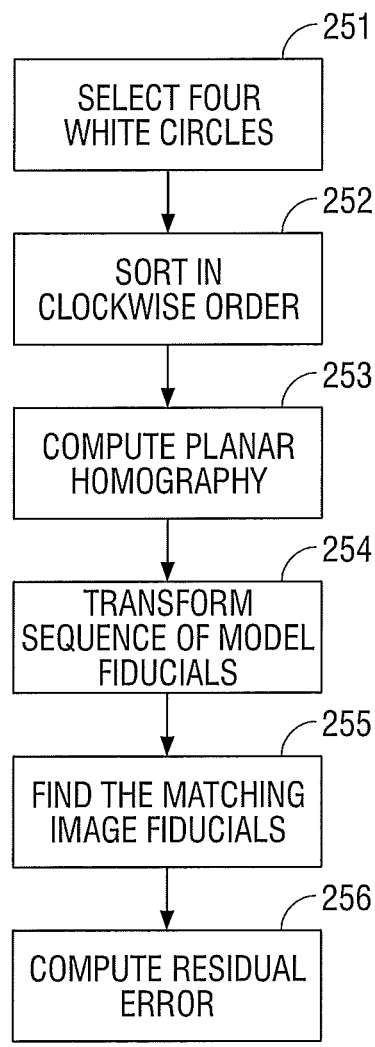
FIG. 21A is a flowchart depicting a correspondence algorithm according to an embodiment of the present disclosure.
Figure 21B:
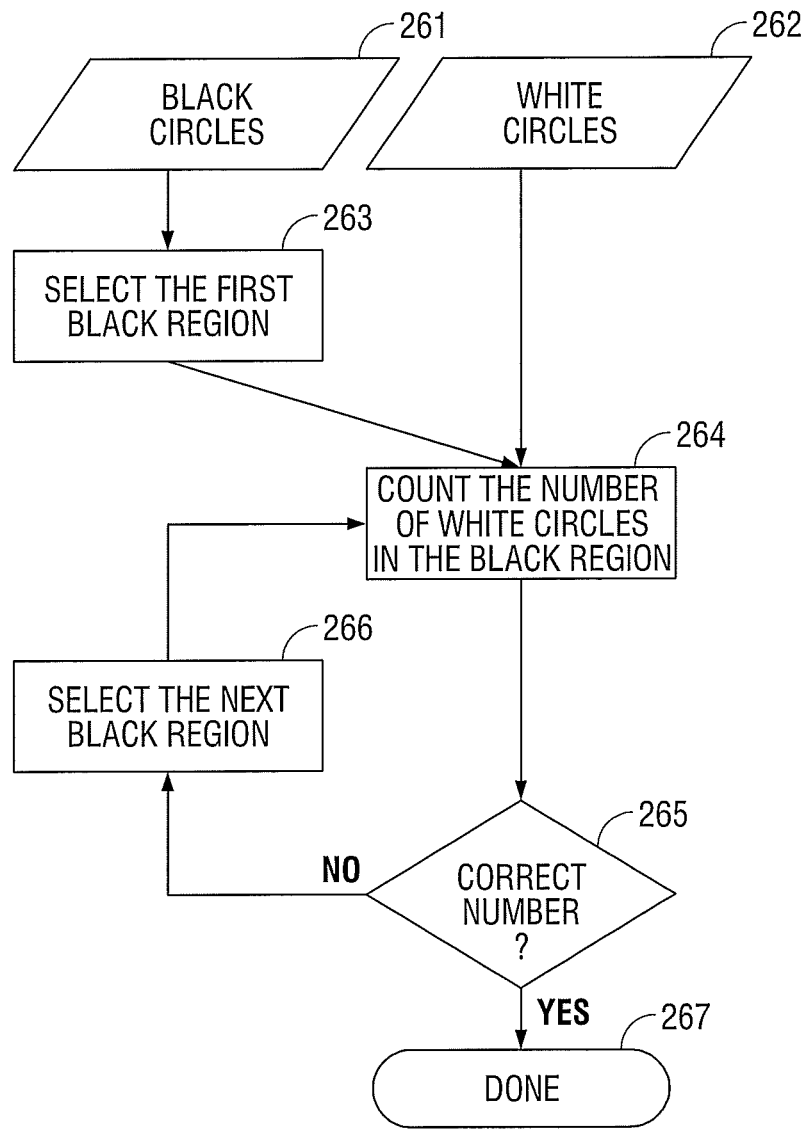
FIG. 21B is a flowchart depicting an algorithm for applying a topology constraint according to an embodiment of the present disclosure.
Figure 22A:
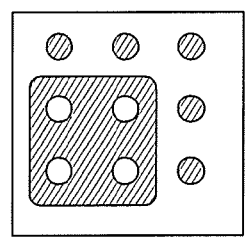
FIG. 22A-22D are a schematic diagrams of fiducial models used in the algorithm of FIG. 21A.
Figure 22B:
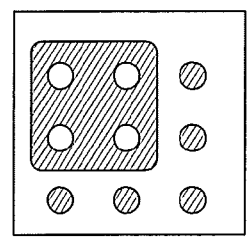
Figure 22C:
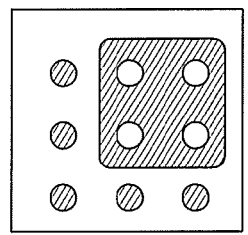
Figure 22D:
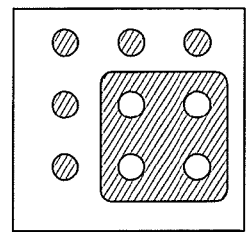

In step 234 of FIG. 15, controller 212 finds a correspondence between the fiducial image and fiducial models using the algorithm of shown in FIG. 21A. In step 251 of FIG. 21A, controller 212 uses a topology constraint to select the four white circles as shown in FIG. 21B. As shown in FIG. 21B, in step 261, controller 212 obtains the black regions stored in step 249 of FIG. 19 and obtains the white circles stored in step 246 of FIG. 17. Controller 212 then selects a first black region in step 263 and counts the number of white circles in the first black region in step 264. Controller 212 determines whether the number of circles in the selected black region matches a predetermined number of circles in step 265. If the number of circles does not match the predetermined number of circles, the algorithm proceeds to step 266 where the next black region is selected and the number of circles in the next black region is counted again in step 264. This process repeats until the number of circles counted in step 264 matches the predetermined number of circles. Once the number of circles counted in step 264 matches the predetermined number of circles, the algorithm proceeds to step 267 where the topology constraint algorithm is completed. In other embodiments, controller 212 selects the four white circles by selecting the four roundest circles.

After the four circles are chosen, they are arranged in a clockwise order using a convex hull algorithm in step 252. The convex hull or convex envelope for a set of points X in a real vector space V is the minimal convex set containing X. If the points are all on a line, the convex hull is the line segment joining the outermost two points. In the planar case, the convex hull is a convex polygon unless all points are on the same line. Similarly, in three dimensions the convex hull is in general the minimal convex polyhedron that contains all the points in the set. In addition, the four matching fiducials in the model are also arranged in a clockwise order.

In step 253, a planar homography matrix is computed. After a planar homography matrix is calculated, the homography matrix is used to transform the fiducial models to image coordinates using the four corresponding fiducial models shown in FIG. 22 to find the closest matching image fiducials (steps 254 and 255). Controller 212 also computes the residual error in step 256. The algorithm uses the resulting 3D transform to transform the 3D fiducial model into the 2D image. It then compares the distances between fiducials mapped into the 2D image with the fiducials detected in the 2D image. The residual error is the average distance in pixels. This error is used to verify accuracy and partly determine the red/green navigation status. Controller 212 then selects the model with the most matches and the smallest residual error. In order for a more accurate result, there has to be a minimum number of black fiducial matches (e.g., three).

In step 235 of FIG. 15, camera pose estimation is performed. The camera pose estimation involves calculating a 3D transform between the camera and the selected model by iteratively transforming the model fiducials onto the fiducial image plane and minimizing the residual error in pixels. The goal is to find the global minimum of the error function. One problem that may occur is the occurrence of significant local minima (e.g., an antenna imaged from the left looks similar to an antenna imaged from the right) in the error function that needs to be avoided. Controller 212 avoids the local minima by performing minimization from multiple starting points and choosing the result with the smallest error. Once the 3D transform is calculated, the controller can use the 3D transform to transform the coordinates of the surgical device 206 to a model space and display the surgical device 206 as virtual surgical device 206a in display 214.

Because object boundaries expand and contract under different lighting conditions, a conventional square corner fiducials location may change depending on lighting conditions. Fiducial patch 204 uses black and white circles, and, thus, is not hampered by this problem because the center of the circle always stays, the same and continues to work well for computing weighted centroids. Other contrasting images or colors are also contemplated.

Figure 23:
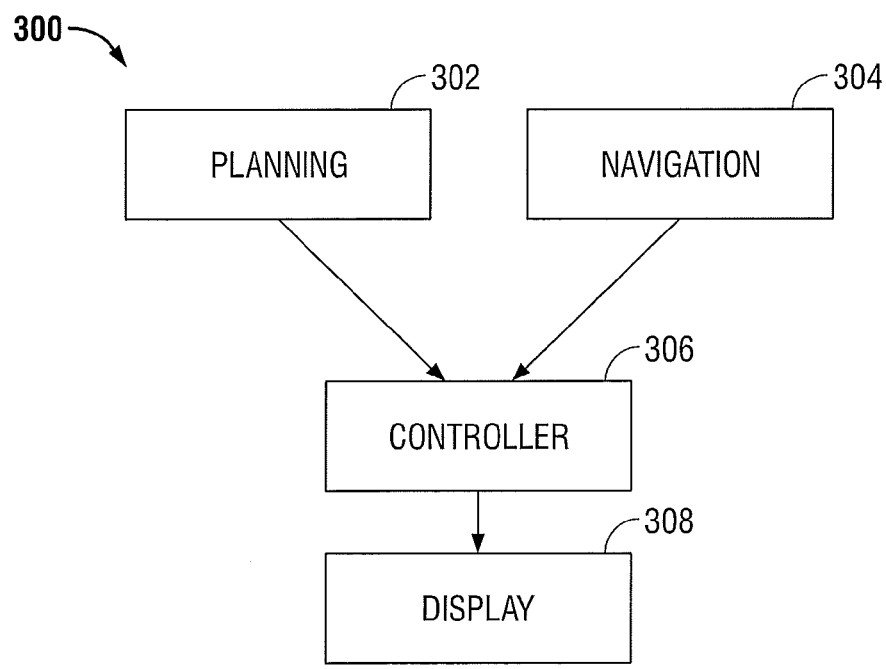
FIG. 23 is a schematic diagram of an integrated planning and navigation system according to another embodiment of the present disclosure.

In another embodiment of the present disclosure, and as shown in FIG. 23, a planning and navigation system 300 is provided. System 300 includes planning system 302 and navigation system 304 that are connected to a controller 306. Controller 306 is connected to a display 308 that may include a single display screen or multiple display screens (e.g., two display screens). Planning system 302 is similar to planning system 100 and navigation system 304 is similar to navigation system 200. In system 300, display 308 displays the planning operation and navigation operation described hereinabove. The planning operation and the navigation operation may be displayed as a split screen arrangement on a single display screen, the planning operation and the navigation operation may be displayed on separate screens, or the planning operation and the navigation operation may be displayed the same screen and a user may switch between views. Controller 306 may import dose settings from the planning system and use the dose setting during a navigation operation to display the ablation zone dimensions.

Figure 26:
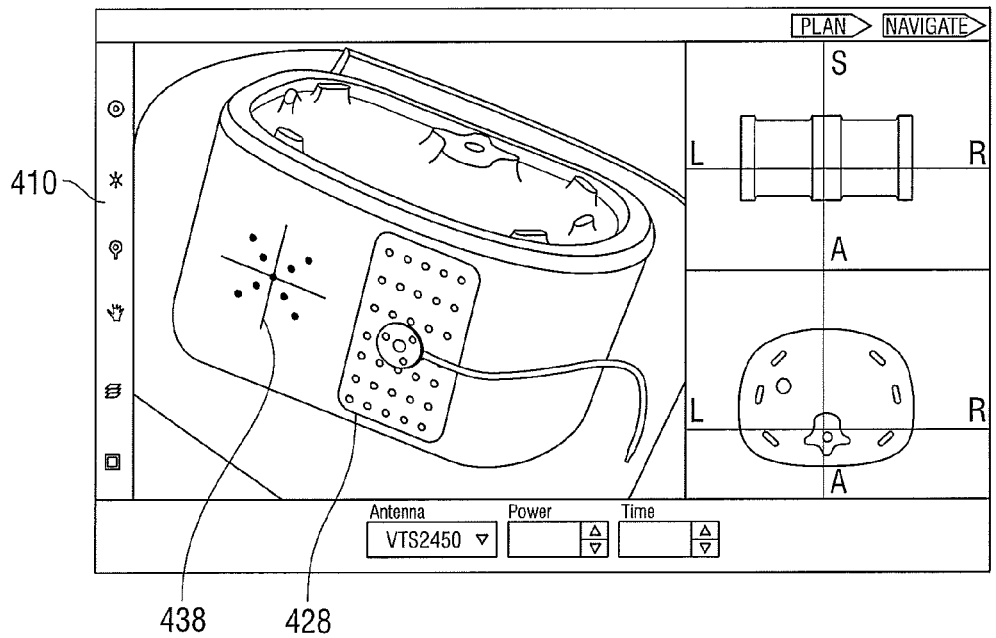
FIGS. 26-29 are schematic diagrams of graphical user interfaces used in the system of FIG. 24 in accordance with various embodiments of the present disclosure.

In other embodiments of the present disclosure, CT navigation and software can be integrated with planning system 100. Turning to FIGS. 24, 25A, and 25B a planning and navigation system is shown generally as 400. System 400 includes an image capturing device 402 that captures CT images of a patient "P" having an electromagnetic reference 428 and/or optical reference 438. The CT images are provided in DICOM format to planning system 404 that is similar to planning system 100. Planning system 400 is used to determine a treatment plan as described above and the treatment plan is provided to controller 408 and displayed as a planning screen 412 on display 410 as shown in FIG. 26.

Navigation system 406 may use an electromagnetic tracking system as shown in FIG. 25A, an infrared tracking system or an optical tracking system as shown in FIG. 25B. Turning to FIG. 25A, a navigation system 420 includes an electromagnetic field generator 422, an surgical device 424 having an electromagnetic transducer 426, and an electromagnetic reference 428 disposed on the patient. The field generator 422 emits electromagnetic waves which are detected by electromagnetic sensors (not explicitly shown) on the surgical device 424 and electromagnetic reference 428 and then used to calculate the spatial relationships between surgical device 424 and electromagnetic reference 428. The spatial relationships may be calculated by the field generator 422 or the field generator 422 may provide the data to controller 408 to calculate the spatial relationship between the ablation needle 424 and the electromagnetic reference 428.

FIG. 25B depicts an alternate navigation system 430 that is similar to the navigation system described in FIG. 13 above. In FIG. 25B, an optical reference or fiducials 438 is placed on a patient. A camera 436 attached to surgical device 424 takes an image of the fiducials 438 and transmits the image to controller 408 to determine a position of the ablation needle in relation to the fiducials 438.

After receiving data from navigation system 406, controller 408 may correlate the position of the surgical device 424 with the CT images in order to navigate the surgical device 424 to a target "T" as described below. In this case, the patient reference (of any type) may have radiopaque markers on it as well to allow visualization during CT. This allows the controller to connect the patient CT image coordinate system to the instrument tracking coordinate system.

Figure 27:
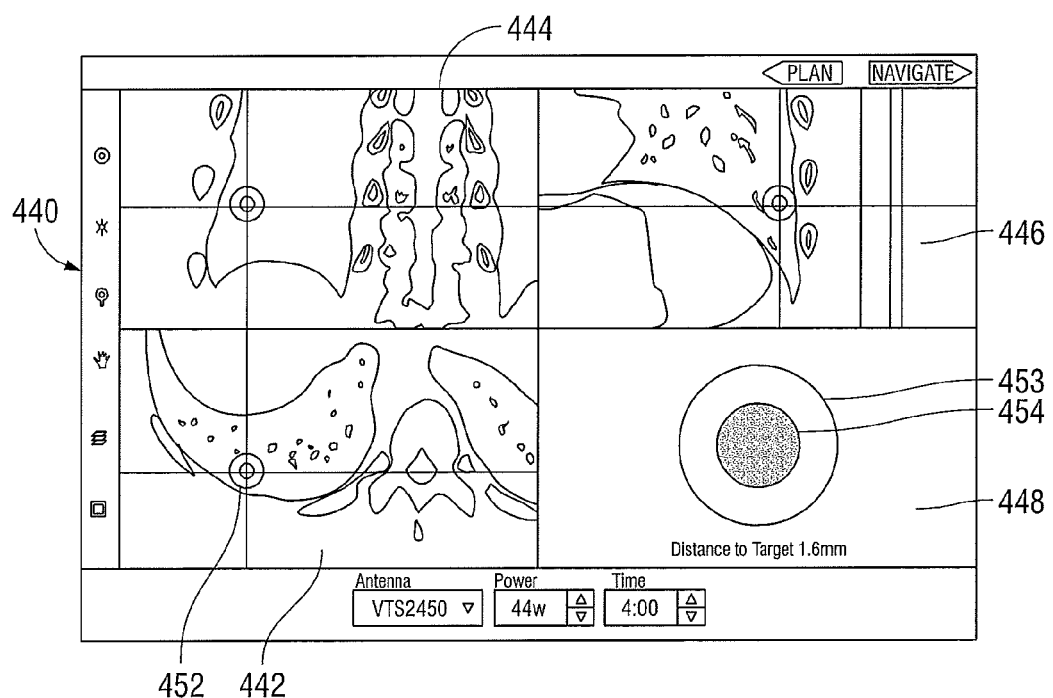

Controller 408 and display 410 cooperate with each other to display the CT images on a navigation screen 440 as shown in FIG. 27. As shown in FIG. 27, display screen 440 includes a transverse view 442, coronal view 444, and sagittal view 446. Each view includes a view of the target "T" and an ablation zone 452 (including a margin). The transverse view 442, coronal view 444 and sagittal view 446, ablation zone 452 are all imported from planning system 404. Additionally, all planning elements (e.g., device selection, energy level, and treatment duration) are automatically transferred to the navigation screen 440. The navigation screen 440 is also a graphical user interface that allows a user to adjust the device selection, energy level, and treatment duration.

A navigation guide screen 448 is provided on display screen 440 to assist in navigating the ablation needle to the target "T". Based on the data received from the navigation system 406, the controller can determine if the surgical device 424 is aligned with target "T". If the surgical device 424 is not aligned with target "T", the circle 454 would be off-centered from outer circle 453. The user would then adjust the angle of entry for the surgical device 424 until the center of circle 454 is aligned with the center of outer circle 453. In some embodiments, circle 454 may be displayed as a red circle when the center of circle 454 is not aligned with the center of outer circle 453 or circle 454 may be displayed as a green circle when the center of circle 454 is aligned with the center of outer circle 453. Additionally, controller 408 may calculate the distance between the target "T" and the surgical device 424.

Figure 28:
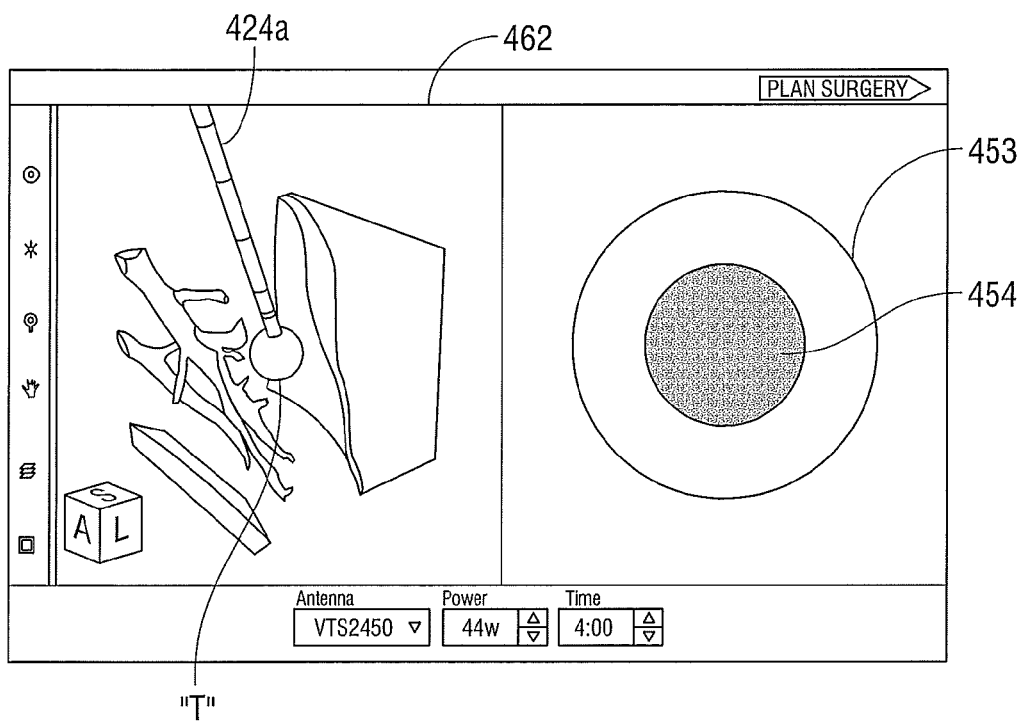

In another embodiment depicted in FIG. 28, controller 408 superimposes a virtual surgical device 424a over a 3D rendered image and displays the combined image on screen 462. Similar to the method described above, a user can align the center of circle 453 with the center of circle 454 to navigate the surgical device 424 to the target "T". Alternatively, the user can determine the position of surgical device 424 in relation to the target "T" by viewing virtual surgical device 424a on screen 462 to navigate the surgical device 424 to the target "T".

Figure 29:
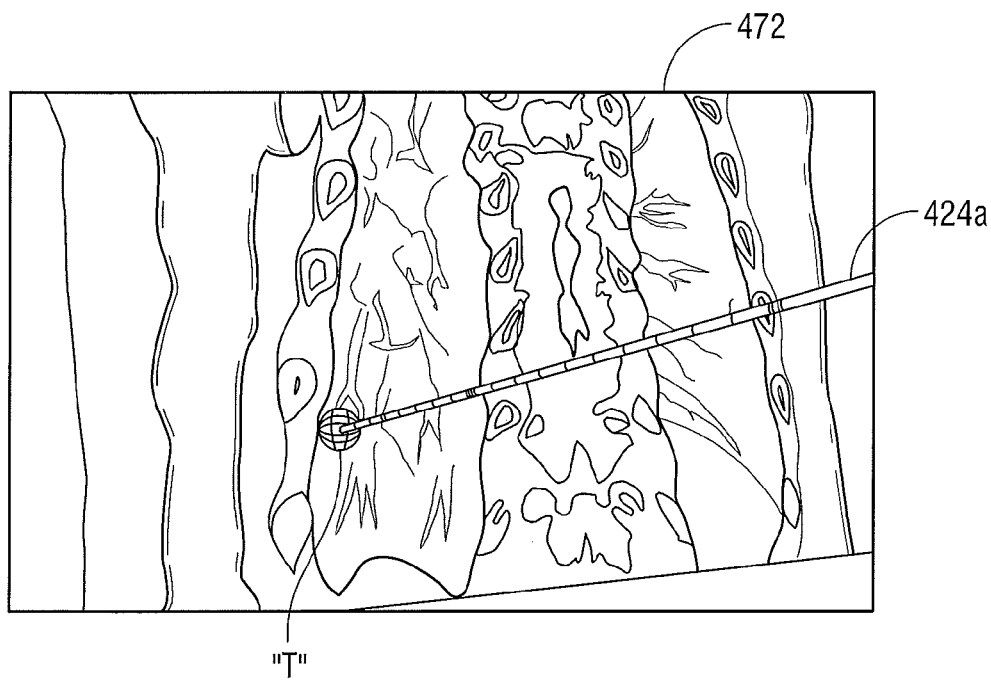

FIG. 29 depicts another embodiment of the present disclosure. Similarly to screen 462 above, in the embodiment of FIG. 29, screen 472 depicts a virtual surgical device 424a in spatial relationship to previously acquired and rendered CT image. The CT image has been volume rendered to demarcate the target "T" as well as additional structures, vessels, and organs. By volume rendering the target "T", as well as the additional structures, vessels, and organs, the user can navigate the surgical device 424 into the patient while also avoiding the additional structures, vessels, and organs to prevent unnecessary damage.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A planning and navigation system, comprising:
   a planning system including:
      a memory configured to store a plurality of images; and
      a first controller configured to render the plurality of images in three dimensions, segment the plurality of images to demarcate a target area, and automatically determine a treatment plan based on the target area; and
   a navigation system including:
      an ultrasound device configured to obtain an ultrasound image in a scan plane, the ultrasound device having a fiducial pattern disposed thereon, the fiducial pattern including a plurality of first unique identifiers disposed in a region and a plurality of second unique identifiers;
      a surgical device having an image capture device configured to capture a fiducial image of the fiducial pattern;
      a second controller configured to:
         receive the ultrasound image and the fiducial image, wherein the controller determines a position of the surgical device in relation to the scan plane based on the fiducial image;
         identify the plurality of first unique identifiers and the plurality of second unique identifiers, wherein the plurality of first unique identifiers includes circles of a first color and the plurality of second unique identifiers includes circles of a second color and wherein identifying includes:
            applying a first threshold to the fiducial image substantially in parallel with applying a second threshold to an inverted fiducial image;
            performing a connected component analysis on the first and second thresholds; and
            applying a geometric filter to results of the connected component analysis to identify the region having the plurality of first unique identifiers and to determine weighted centroids of the plurality of first unique identifiers and the plurality of second unique identifiers; and
         correspond the fiducial image to a model image by:
            selecting a plurality of the circles of the first color;
            determining an amount of the circles of the first color disposed in a first portion of the region of the fiducial pattern;
            determining whether the determined amount of the circles of the first color disposed in the first portion matches a predetermined amount of the circles of the first color; and
            in response to a determination that the determined amount of the circles of the first color disposed in the first portion does not match the predetermined amount of the circles of the first color, determining an amount of the circles of the first color disposed in a second portion of the region of the fiducial pattern; and a third controller configured to receive the rendered plurality of images, the target area, the treatment plan, the ultrasound image, and the position of the surgical device in relation to the scan plane; and a display configured to:
  display a first display having the rendered plurality of images, the target area, and the treatment plan; and
  display a second display having the ultrasound image, a virtual image of the surgical device based on the position of the surgical device in relation to the scan plane, and the treatment plan.

2. The planning and navigation system of claim 1, wherein the first display and the second display are displayed on a single screen.

3. The planning and navigation system of claim 2, wherein the first display and second display are displayed simultaneously.

4. The planning and navigation system of claim 2, wherein a user can switch between the first display and the second display.

5. The planning and navigation system of claim 1, wherein the display has two screens and the first display is displayed on a first screen and the second display is displayed on a second screen.

6. The planning and navigation system of claim 1, wherein the first controller performs a volumetric analysis to determine the treatment plan.

7. The planning and navigation system of claim 1, further comprising an input device configured to adjust the treatment plan.

8. The planning and navigation system of claim 1, wherein the display provides a graphical user interface.

9. The planning and navigation system of claim 1, wherein the first controller segments at least one vessel and adjusts the treatment plan based on the proximity of the at least one vessel to the target area.

10. The planning and navigation system of claim 1, wherein the first controller segments at least one organ and adjusts the treatment plan based on a position of the target area in relation to the at least one organ.

11. The planning and navigation system of claim 1, wherein the fiducial pattern is affixed to a known location on the ultrasound device.

12. The planning and navigation system of claim 1, wherein the image capture device is affixed to a known location on the surgical device.

13. The planning and navigation system of claim 1, wherein the region is of the second color.

14. The planning and navigation system of claim 1, wherein the second controller estimates a camera pose, and transforms the surgical device to model coordinates.

15. The planning and navigation system of claim 1, wherein the selected plurality of the circles of the first color is selected based on roundness of the circles of the first color.

16. The planning and navigation system of claim 1, wherein corresponding the fiducial image to the model image further includes:
  sorting the selected plurality of the circles of the first color;
  computing a planar homography matrix;
  transforming the model image; and
  identifying matching image fiducials.

* * * * *